United States Patent [19]

Smith et al.

[11] Patent Number: 4,828,986
[45] Date of Patent: May 9, 1989

[54] ASSAY METHOD AND DIAGNOSTIC SYSTEM FOR DETERMINING THE RATIO OF APO B-100 TO APO A-I IN A BLOOD SAMPLE

[75] Inventors: Richard S. Smith, Del Mar; Doreen M. Hogle, San Diego; Linda K. Curtiss, San Diego; Joseph L. Witztum, San Diego; Steven Young, San Diego, all of Calif.

[73] Assignee: Scripps Clinic and Research Foundation, La Jolla, Calif.

[21] Appl. No.: 913,140

[22] Filed: Sep. 29, 1986

[51] Int. Cl.$^4$ .............................................. G01N 33/53
[52] U.S. Cl. .......................................... 435/7; 435/68; 435/172.2; 435/240.27; 435/810; 435/948; 436/518; 436/548; 530/387; 530/809; 935/106; 935/108; 935/110
[58] Field of Search ..................... 436/518, 548; 435/7, 435/810, 68, 172.2, 240.27, 948; 935/106, 108, 110; 530/387, 809

[56] References Cited

U.S. PATENT DOCUMENTS 4,376,110  3/1983  David et al. .
4,677,057  6/1987  Curtiss et al. ........................ 436/533

OTHER PUBLICATIONS

American Type Culture Collection Catalogue of Cell Lines and Hybridomas, Fifth Edition, 1985, p. 149.

Primary Examiner—Robert J. Warden
Assistant Examiner—Stephen C. Wieder
Attorney, Agent, or Firm—Dressler, Goldsmith, Shore, Sutker & Milnamow, Ltd.

[57] ABSTRACT

Methods of determining the ratio of apolipoprotein B-100 to apolipoprotein A-I using ELISA techniques in conjunction with monoclonal paratopic molecules are disclosed as are diagnostic systems useful in performing those determinations. Monoclonal paratopic molecules secreted by hybridomas having ATCC accession numbers HB 8742, HB 8746, HB 9200 and HB 9201 are utilized.

13 Claims, 4 Drawing Sheets

ASSAY METHOD AND DIAGNOSTIC SYSTEM FOR DETERMINING THE RATIO OF APO B-100 TO APO A-I IN A BLOOD SAMPLE

TECHNICAL FIELD

The present invention relates to an assay method for a marker for abnormal lipid metabolism, and particularly to an assay method for determining the ratio of apolipoprotein B-100 to apolipoprotein A-I in a liquid blood sample as well as to a diagnostic system for carrying out that method.

BACKGROUND OF THE INVENTION

A. Atherosclerosis and Lipoproteins

Atherosclerosis is the disease in which cholesterol and other lipids, accumulating on the walls of arteries, form bulky plaques that inhibit the flow of blood and may lead to the formation of a clot, obstructing an artery and causing occlusive thrombotic or embolic disease such as a heart attack or stroke. Up to 50 percent of all deaths in the United States are caused by atherosclerosis and its secondary complications.

Human atherosclerosis is defined as the accumulation of selected lipids, including cholesterol, and cells in the walls of arteries and with time produces occlusive lesions. Although the etiology of atherosclerosis is multifactorial, a large body of clinical, pathologic, genetic and experimental evidence suggests that abnormalities of lipoprotein metabolism can contribute to the development of atherosclerosis. These lipids are carried in the blood stream as lipid-protein complexes called lipoproteins.

Atherosclerosis, and particularly that form known as coronary artery disease (CAD), is a major health problem. Atherosclerosis and its related vascular diseases accounted for 983,000 deaths in 1983; and CAD alone accounts for more deaths annually than all forms of cancer combined. In the United States, more than 1 million heart attacks occur each year and more than five hundred thousand people die as a result of this disease. In direct health care costs, CAD costs the United States more than $60 billion a year. This enormous toll has focused attention on ways to identify particular populations at risk for CAD so that the disease can be controlled with diet, behavioral modification (exercise), and specific therapeutic agents.

Four major classes of cholesterol-associated plasma lipoprotein particles have been defined, and have their origin in the intestine or liver. These particles are involved in the transport of the neutral lipids including cholesterol and triglycerides. All classes of plasma lipoproteins have apolipoproteins associated with the lipid-protein complex; and the apolipoproteins play requisite roles in the function of these lipoproteins.

The first class is the chylomicrons. They are the largest of the lipoproteins and are rich in triglycerides. The site of origin of the chylomicrons is the intestine.

Whereas apolipoproteins are a quantitatively minor proportion of the mass of chylomicrons, apolipoproteins A-I, A-II and A-IV are reportedly significantly associated with chylomicrons, and intestinal synthesis of these A apolipoproteins has been found. Chylomicrons also contain apolipoprotein B-48. Much of the chylomicron complement of A apolipoproteins is lost, and C and E apolipoproteins are acquired when chylomicrons are exposed to plasma or high density lipoprotein (HDL) in vitro. Intestinal production of the A apolipoproteins (apo A) may be regulated by factors other than fat absorption and chylomicron formation.

The next class of lipoproteins is the very low density lipoproteins, VLDL. The VLDL particle is made in the liver and is involved in triglyceride metabolism and transport of these lipids from the liver. The apolipoproteins apo B-100 and apo E are the major constituents of the VLDL particle.

The third lipoprotein is called low density lipoprotein (LDL), and is a specific product of the catabolism of VLDL. The predominant apolipoprotein in the LDL particle is apolipoprotein B-100, or apo B-100.

The results of the now classic Framingham study (1971) showed a clear correlation between risk for CAD and serum cholesterol levels. This study also demonstrated that elevated levels of low density lipoprotein (LDL) cholesterol are associated with increased risk of CAD. Recently, a study conducted by the Lipid Research Clinics Coronary Primary Prevention Trial (1984) has demonstrated that plasma levels of cholesterol and LDL cholesterol can be reduced by a combined regime of diet and drugs, and that this reduction of plasma cholesterol results in reduction of the incidence of CAD mortality.

LDL is the major cholesterol-carrying lipoprotein in plasma. LDL is a large spherical particle whose lipid core is composed of about 1500 molecules of cholesterol, each attached by an ester linkage to a long chain fatty acid. This core of cholesteryl esters is enclosed by a layer of phospholipid, unesterified cholesterol molecules, and a single molecule of apolipoprotein B-100. The phospholipids are arrayed so that the hydrophilic heads are on the outside, allowing the LDL to be in hydrated suspension in the blood or extracellular fluids.

The cholesterol is delivered to cells on LDL via a specific LDL receptor, and is liberated from the LDL particles in lysosomes where it can control the cell's cholesterol metabolism. An accumulation of intracellular cholesterol modulates three processes.

First, it reduces the cell's ability to make its own cholesterol by turning off the synthesis of an enzyme, HMG CoA reductase, that catalyzes a step in cholesterol's biosynthetic pathway. Suppression of the enzyme leaves the cell dependent on external cholesterol derived from the receptor-mediated uptake of LDL.

Second, the incoming LDL-derived cholesterol promotes the storage of cholesterol in the cell by activating an enzyme denominated lipoprotein acyltransferase. That enzyme esterifies fatty acids to excess cholesterol molecules, making cholesteryl esters that are deposited in storage droplets.

Third, and most significant, the accumulation of cholesterol within the cell drives a feedback mechanism that makes the cell stop synthesizing new LDL receptors. Cells thereby adjust their complement of external receptors so that enough cholesterol is brought into the cells to meet the cells' varying demands but not enough to overload them. For example, fibroblasts that are actively dividing, so that new membrane material is needed, maintain a maximum complement of LDL receptors of about 40,000 per cell. In cells that are not growing, the incoming cholesterol begins to accumulate, the feedback system reduces receptor manufacture and the complement of receptors is reduced as much as tenfold.

On the other hand, it has been shown that another circulating lipoprotein, high density lipoprotein (HDL)

particle is implicated in a state of elevated cholesterol associated with lowered risk of atherosclerosis. Apolipoprotein A-I is a structural protein and antigen of the HDL particle. The amount of HDL provides an inverse correlation with the predicted incidence of atherosclerosis.

High density lipoprotein (HDL) contains two major apolipoproteins, apolipoprotein A-I (apo A-I) and apolipoprotein A-II (apo A-II). Apo A-I is the major protein component of all primate HDL. All HDL particles contain apo A-I, and therefore immunoquantification of HDL has usually involved the quantitation of apo A-I. About 80% of HDL particles also contain apo A-II, but HDL particles containing only apo A-II have not been described.

One function of apo A-I is the activation of the plasma enzyme, lecithin-cholesterol acyltransferase (LCAT). This enzyme is required for the esterification of free cholesterol on HDL for transport to the liver. In the absence of apo A-I, cholesterol in the blood is not esterified and thus cholesterol is not cleared from the blood. The specific role in HDL metabolism served by apo A-II has not been defined.

Many studies have shown that elevated HDL levels correlate with a reduced incidence of CAD. Some authors have speculated that HDL removes cholesterol from peripheral sites, such as the arterial wall, therefore attributing anti-atherogenic properties to HDL. Higher concentrations of HDL cholesterol are correlated with relatively normal lipid metabolism and a lower incidence of and/or a decreased severity of cardiovascular disease, whereas elevated levels of LDL cholesterol are associated with abnormal lipid metabolism and an increased risk of CAD. For the proper management of patients with hyperlipidemia (excess lipids in the blood) and those patients at special risk for CAD, it is desirable to frequently determine levels of LDL and HDL cholesterol. To date, assays of HDL cholesterol have been cumbersome and inaccurate in determining blood levels of HDL.

B. Lipoprotein Structure and Function

It is important to understand that cholesterol does not exist free in plasma but is transported to tissue sites in the body by lipoproteins. Cholesterol can be obtained from directed cellular synthesis or by diet. However, cholesterol can be removed from the host only by the liver, where it is converted to bile acids and excreted.

Chylomicrons carry dietary cholesterol and triglycerides to the liver for subsequent processing, whereas, LDL delivers cholesterol to extrahepatic tissues, including the coronary arteries. Hence, the lipoprotein, LDL/apo B-100, is involved in the deposition of "bad" cholesterol to peripheral tissue. Conversely, the lipoprotein, HDL/apo A, removes "good" cholesterol from the tissues and returns cholesterol to the liver for excretion.

Historically, many systems have been developed to isolate and to characterize lipoproteins. These techniques are usually based upon the physicochemical properties of the lipoprotein particles. The two most frequently used techniques are ultracentrifugation and electrophoresis.

Differential density gradient ultracentrifugation takes advantage of the fact that the lipoproteins are lighter or less dense than other plasma proteins, and it is relatively easy, though time-consuming and cumbersome, to separate the chylomicrons (the lightest lipoproteins), VLDL, LDL and HDL from each other. Electrophoretic techniques have been useful for the classification of patients with hyperlipidemias. However, these techniques are not easily carried out in an ordinary clinical laboratory.

One also can see that the simple quantitation of blood cholesterol or triglycerides does not provide the physician with the information about which specific lipoproteins are carrying these lipids and their quantitation.

C. The Plasma Lipoproteins

Four major classes of plasma lipoproteins; i.e., chylomicrons, VLDL, LDL and HDL, have been defined, and subclasses within these undoubtedly exist. All lipoproteins have their origin in the intestine or liver, or both, and appear to have a pseudomicellar structure. Neutral lipids, and particularly, cholesterol esters and triglycerides, are maintained in the core of the lipoproteins in a soluble and stable form through interactions with the surface polar constitutents, apolipoproteins and phospholipids.

Unesterified cholesterol also is present in these complexes. Its polarity lies between that of the neutral lipids (cholesteryl esters and triglycerides) and that of the more polar apolipoproteins and phospholipids and can be found both in the core and the surface.

An outer surface consisting of apolipoproteins, unesterified cholesterol, and phospholipids surrounds a water-insoluble core of cholesteryl esters and triglycerides, protecting the apolar lipids from the aqueous environment. This general structural concept has been supported by low-angle x-ray scattering studies and by other physical methods in which a variety of probes have been used to explore the structure of the lipoproteins. An important function of the plasma lipoproteins is thus the solubilization and transport of the neutral lipids.

D. The Apolipoproteins

Apolipoproteins are the lipid-free protein components of the plasma lipoproteins obtained by treating isolated intact lipoproteins with organic solvents, detergents, or chaotropic agents. Not all proteins captured with lipoproteins necessarily have a role in lipid transport. A pertinent example is the recent recognition that the serum amyloid A proteins, acute phase reactants, are transported in plasma bound to HDL. These low molecular weight proteins may comprise up to 30 percent of apo-HDL in inflammatory states, but it is doubtful that they have specific lipid transport roles.

1. Apolipoprotein A-I

(a) The Protein

The apolipoprotein A-I (apo A-I) is a protein of interest in the present invention. Apo A-I is discussed below.

Apo A-I is the major protein component of all primate HDL, is present in all HDL particles, and there are multiple, e.g. 7-8, apo A-I molecules per HDL particle. It has been reported to be present in relatively minor amounts in chylomicrons, VLDL and LDL as well as constituting about 60-80 percent of the total protein mass of HDL.

Apo A-I consists of a single chain of 243 to 245 residues; does not contain cystine, cysteine, leucine, or carbohydrate; and exists in several isoforms. Apo A-I has an alpha helical content of about 55 percent in the lipid-free state, which increases to about 75 percent upon binding phospholipid. Repeating cycles of 11 helical residues have been identified in this apolipoprotein. It has been suggested that these units represent a single ancestral chain which, by gene duplication, has generated a 22-residue repeat unit. These units have close sequence homology and are believed to represent the lipid-binding regions of the protein.

Apo A-I is a potent activator of LCAT, a plasma enzyme that catalyzes the conversion of cholesterol and phosphatidylcholine to cholesteryl ester and lysophosphatidylcholine, respectively. Specific lipid-binding regions of apo A-I have been found to activate LCAT, and this activity has been associated with the property of lipid binding. As already noted, liver and intestine synthesize apo A-I, but their relative contributions to the total plasma content and the factors modulating apo A-I production are not well defined.

Typically, more than about 90 percent of plasma apo A-I is associated with HDL, less than about 1 percent with VLDL and LDL, and about 10 percent or less is associated with the lipoprotein-free fraction of plasma. The amounts of apo A-I in each particle type differs with those who report the data and appears to be a functon of the techniques used in separation of the particles.

(b) Clinical Importance of Apo A-I Lipoproteins

Measurement of the major protein constituent of HDL, apo A-I, is clinically important. The results of a number of studies have demonstrated that apo A-I levels are decreased in subjects with CAD. This observation stresses the protective role of plasma apo A-I in this patient group.

The results of several studies suggest that by measuring the apo A-I level accurately, it may be possible to predict an individual's prognosis for abnormal lipid metabolism, atherosclerosis, and specifically for CAD. For a recent survey of 2416 children, See Freedman et al. (1986) *New Eng. J. Med.* 315:721–726. However, the amount of apo A-I alone has not been capable of utilization as a marker for abnormal lipid metabolism if only because of its difficulty in accuracy and precision of measurement. Thus, while relatively high apo A-I levels tend to correlate with normal lipid metabolism and relatively low levels with abnormal lipid metabolism and CAD, a clear line of demarcation between normal persons and those with known CAD has not been reported.

As noted before, apo A-I has been found extremely difficult to accurately and precisely quantify in a clinically useful immunoassay system such as a radioimmunoassay (RIA), an enzyme-linked immunoassay (ELISA), an electroimmunoassay (EIA), a radial immunodiffusion (RID) or by immunonephelometry (INA). See, for example, Table 1 of Steinberg et al. (1983) *Clin. Chem.* 29/3:415–426 for the variance in values reported using various techniques.

One of the reasons alleged for these analytical difficulties is that the apolipoprotein A-I molecule is present in plasma and serum as part of a large, biochemically heterogeneous particle, within which some of the antigenic sites (epitopes) are concealed and masked. As a consequence, several workers have utilized unmasking treatments for their samples so that the normally concealed epitopes are unmasked, and available for immunoreaction.

Steinberg et al. (1983) *Clin. Chem.* 29: 415–426 also discuss unmasking by treatment of a blood sample such as plasma or serum with denaturing agents such as urea, tetramethyl urea and guanidine, surfactants such as sodium dodecyl sulfate and polyoxyethylene (20) sorbitan monolaurate (Tween 20), heating as at 52 degrees C. for 3 hours and at 37 degrees C. for 2 hours, and delipidating organic solvents such as mixtures of ethanol and diethyl ether, methanol and diethy ether, chloroform and methanol, and the like. Additional specific unmasking treatments can be found in the work reported by Maciejko et al. (1982) *Clin. Chem.* 28:199–204 (surfactant); Koren et al. (1985) *Clin. Chim. Acta* 147;85–95 (organic solvent); and Bury et al. (1985) *Clin. Chem.* 31:247–251 (37° C., 2 hours).

Some of the above workers and others have also utilized polyclonal antibody preparations to help avoid the apparent heterogenicity of apo A-I as it exists in plasma and serum. Maciejko et al. (1982) *Clin. Chem.* 28:199–204; Koren et al. (1985) *Clin. Chim. Acta* 147:85–95; Bury et al. (1985) *Clin. Chem.* 31:247–251; and Fesmire et al. (1984) *Clin. Chem.* 30:712–716. Of course, the use of polyclonal antibodies in a clinically useful quantitative immunoassay carries with it the detriment of differences in antibody activity attendant in use of sera from several animals, and also differences in immunospecificity from different batches of serum.

On the other hand, aside from the monoclonal paratopic molecules utilized herein, no other workers have described monoclonal antibodies that immunoreact substantially equally with HDL particles and apo A-I, as well as immunoreact with substantially all of the apo A-I present on HDL in a sample. Thus, Curtiss et al. (1985) *J. Biol. Chem.* 200:2982–2998 reported one monoclonal antibody designated AI-7 that immunoreacted about equally with apo A-I and HDL, but was capable of immunoprecipitating only about 60 percent of radiolabeled apo A-I or HDL known to be present in the samples assayed.

2. Apolipoprotein B-100

(a) The Protein

A species of apo B synthesized in the liver, termed apolipoprotein B-100 (apo B-100), is recognized and bound by cellular LDL receptors. By binding apo B-100, these receptors bind LDL particles and extract them from the plasma. The LDL is thereby taken into the cells and broken down, yielding its cholesterol to serve each cell's needs. The apo B-LDL receptor interaction thus plays a major role in removal of LDL cholesterol from the bloodstream, and all LDL particles contain apo B-100.

(b) Clinical Importance of Apo B-100 Lipoprotein

Contrary to apo A-I and HDL, higher levels of apo B have been associated with abnormal lipid metabolism and CAD, whereas lower amounts tend to correlate with normalcy and a lowered risk of the disease. Chylomicron particles contain a major apo B protein that is referred to as apolipoprotein B-48, which is also a product of the apo B-100 gene [Young et al. (1986) *J. Biol. Chem.* 261:2995–2998] and shares at least one cross-reactive epitope with apo B-100. VLDL and LDL particles contain apo B-100. Of the two proteins apolipoprotein B-100 (apo B-100) appears to be the more important to abnormal lipid metabolism and CAD.

Recently, several investigators have suggested that plasma levels of apo B-100 may be more predictive of CAD risk than plasma LDL cholesterol levels. Sniderman et al. (1980) *Proc. Natl. Acad. Sci. U.S.A.* 77:604–608. As was the case for HDL and apo A-I, no clear line of demarcation has been determined from the level of apo B-100 or LDL alone that can identify a person as having abnormal lipid metabolism or being at an increased risk of CAD.

Many types of immunoassays for plasma apoprotein B utilizing specific antibody-containing antisera have been reported, including competitive fluid phase and solid phase RIAs, ELISAs, RIDs and others. Problems limiting the widespread application of these apo B immunoassays have been reproducibility, and the quality and specificity of the antisera used. Reviews of the methodological problems of each of the various types of apo B assays are found in Currey et al. (1978), *Clin. Chem.* 24:280–286 and Rosseneu et al. (1983), *Clin. Chem.* 28:427–433.

Several investigators have reported development of panels of monoclonal antibodies against human apo B for use in studying its antigenic structure and role in lipoprotein metabolism. Furthermore, there have been reports of using anti-apo B monoclonal antibodies to measure plasma apo B levels in fluid-phase RIA's. Patton et al. (1983) *Clin. Chem.* 29:1898–1903; Maynard et al. (1984) *Clin. Chem.* 30:1620–1624 and Young et al., (1986) *Clin. Chem.* 32:1484–1490. In addition, one group has reported use of a mixture of anti-apo B monoclonal antibodies in a radial immunodiffusion assay for plasma apo B. Marconvina et al. (1985) *Clin. Chim. Acta* 147:117–125. However, these assay techniques suffer from the necessity of lengthy incubations, repeated centrifugation and/or use of radioactive materials.

3 Monoclonal Paratopic Molecules as Reagents for Apo A-I and B-100

The use of monoclonal antibodies or their antibody combining site portions; i.e., paratopic molecules, as reagents for assaying for the presence of apo A-I or B-100 in human blood samples is attractive because once obtained, such reagents can be produced in relatively large amounts with consistent quality, and thus avoid the inconsistency problem associated with polyclonal antibodies. However, there are a number of factors that militate against the use of a particular monoclonal paratopic molecule as a component in such assay systems.

Using a monoclonal antibody as exemplary of a monoclonal paratopic molecule, the art teaches that a monoclonal antibody can be too immunospecific to be useful because of the antigenic heterogeneity of its target antigen. For example, the specificity of conventional polyclonal antibody-containing antisera depends on a consensus of hundreds of thousands of different antibodies that bind to antigenic determinants covering most or all of an antigenic protein, as has been found useful in apo A-I assays. As a result, small changes in the structure of the antigen due to genetic polymorphism, heterogeneity of glycosylation or slight denaturation or other reaction will usually have little effect on polyclonal antibody binding. Similarly, a larger or smaller subset of antibodies from polyclonal antisera will usually bind antigens that have been modified or denatured.

In contrast, monoclonal antibodies usually bind to one antigenic determinant (epitope) on the antigen molecule. If, for any reason, that determinant is altered, the antibody may or may not continue to bind. Whether this is a problem or an advantage depends on the individual circumstances. If, as in the present case, the monoclonal antibody is to be used in a diagnostic assay for an apolipoprotein, a minor antigenic variation in that protein could cause gross errors. Thus, for example, Tsao et al. (1982) *J. Biol. Chem.* 257:15222–15228 and Mao et al. (1983) 29:1890–1897 reported that some monoclonal antibodies specific for apo B molecules bind to epitopes that are not expressed on all LDL particles. Such antibodies would clearly not be useful for quantifying total apo B-100 in plasma or serum.

The antigenic heterogeneity of apoproteins A-I was discussed before. Heterogeneity of apo -100 is also well documented. For instance, epitope expression on apo B has been found to be modulated by (1) the composition of the associated lipids, (2) temperature of the immunoreaction, (3) the degree of isolation of LDL from its native environment, and (4) genetic expression between individuals.

Second, because of their unique specificity, the successful use of a monoclonal antibody (Mab) is often dependent on its affinity for the target antigen. For instance, whereas a Mab may have sufficient affinity to be useful in binding liquid and solid phase antigen while the Mab is itself in the liquid phase, that same antibody may not be useful as a solid phase-bound antibody that is useful in binding to and retaining the antigen from solution.

The above problems are generic to the use of monoclonal antibodies. Those skilled in the art have therefore recognized that it is essential to test and characterize monoclonal antibodies in any assay system in which they are to be used. See Goding, James W., *Monoclonal Antibodies: "Principles and Practice"*, Academic Press, New York (1983), pages 40–46.

BRIEF SUMMARY OF THE INVENTION

The present invention is directed to an improved method for assaying for a marker of abnormal lipid metabolism, as well as to a diagnostic system, typically in kit form, for carrying out that method. In such an assay the amounts of apolipoprotein B-100 and apolipoprotein A-I in a unit volume of a person's blood sample are measured, and the ratio of apolipoprotein B-100 to apolipoprotein A-I is determined as a unitless number.

The present improvement comprises assaying a first aliquot of an apolipoprotein B-100-containing human liquid blood sample for the amount of apolipoprotein B-100 by admixing the first liquid sample aliquot with a solid support that consists essentially of the solid matrix having solid phase-bound first monoclonal paratopic molecules that immunoreact with apolipoprotein B-100 and are secreted by one of the hybridomas having ATCC accession numbers HB 8742 or HB 8746 to form a solid-liquid phase admixture. The surface of the solid support having blocked non-specific protein binding sites. That admixture is maintained under biological assay conditions for a predetermined period of time that is sufficient for the first paratopic molecules to immunoreact with apolipoprotein B-100 present in the sample aliquot and form a solid phase-bound immunoreactant that contains substantially all of the apolipoprotein B-100 present in the sample aliquot.

The apolipoprotein B-100 in the first liquid sample aliquot described above also is admixed with liquid phase second monoclonal paratopic molecules that immunoreact with apliproprotein B-100, are secreted by one of the hybridomas having ATCC accession numbers HB 8742 or HB 8746 but are not utilized in the previous admixing steps; i.e., monoclonal paratopic molecules secreted by the other of the two above hybridomas that are not used as solid phase-bound paratopic molecules, and are operatively linked to an enzyme indicating means to form a second admixture. That second admixture is maintained under biological assays conditions for a predetermined period of time sufficient for the second paratopic molecules to form an immunoreactant with substantially all of the apolipoprotein B-100 present in the sample aliquot. The solid and liquid phases resulting after admixture of both paratopic molecules, and the formation of immunoreactants are separated and the amount of indicating means-linked apolipoprotein B-100-containing immunoreactant present in the separated solid phase, and thereby the amount of apolipoprotein B-100 in a unit volume of the sample, is determined.

In a preferred embodiment, the two above admixing steps are carried out substantially simultaneously, and the two maintaining steps are carried out together. Thus, the first paratopic molecules and the second, enzyme-linked paratopic molecules are admixed with the sample substantially simultaneously, and the resulting solid-liquid phase admixture is maintained for a period of time that is sufficient for both paratopic molecules to immunoreact with substantially all of the apolipoprotein B present in the sample.

A second aliquot of the person's liquid blood sample that contains apolipoprotein A-1 and is free from unmasking treatment is utilized in the second assay. Here, the second liquid sample aliquot is admixed with the solid support that consists essentially of a solid matrix having solid phase-bound third monoclonal paratopic molecules that immunoreact with an apolipoprotein A-I and are secreted by one of the hybridomas having ATCC accession numbers HB 9200 or HB 9201 to form a third solid-liquid phase admixture. The surface of the solid support again having blocked non-specific protein binding sites. The third solid-liquid phase admixture is maintained under biological assay conditions for a predetermined time period that is sufficient for the third paratopic molecules to immunoreact with substantially all apolipoprotein A-I present in the sample aliquot and form a solid-phase bound immunoreactant that contains substantially all apolipoprotein A-I present in the sample aliquot.

The same, second liquid sample aliquot containing apolipoprotein A-I is admixed with liquid phase fourth monoclonal paratopic molecules that immunoreact with apolipoprotein A-I, are secreted by one of the hybridomas having ATTC accession numbers HB 9200 or HB 9201 but are not utilized in the previous admixing step; i.e., the paratopic molecules other than those used as a portion of the solid and are operatively linked to an enzyme indicating means to form a fourth admixture. The fourth admixture is maintained under biological assay conditions for a predetermined period of time that is sufficient for the fourth, indicating means-linked paratopic molecules to form an immunoreactant with substantially all apolipoprotein A-I present in the sample aliquot. The solid and liquid phases that results after admixture of both of the above paratopic molecules and the formation of immunoreactants are separated, and the amount indicating means-linked apolipoprotein A-I-containing immunoreactant present in the separated solid phase, and thereby the amount of apolipoprotein A-I in a unit volume of sample, is determined.

It is preferred also that the two above admixing steps be carried out substantially simultaneously and that the above two maintaining steps be carried out together. Thus, again, the solid phase-bound paratopic molecules, the enzyme-linked paratopic molecules and the sample aliquot are admixed substantially simultaneously together and maintained until the solid and liquid phases are separated.

In particularly preferred embodiments, the above assays for apolipoprotein B-100 and apolipoprotein A-I are carried out utilizing the preferred embodiments so that in each assay, the solid phase-bound monoclonal paratopic molecules, the liquid phase enzyme indicating means-linked monoclonal paratopic molecules and the sample aliquot are admixed substantially simultaneously and then maintained for the period of time sufficient for both paratopic molecules in each admixture to immunoreact with substantially all of the respective apolipoproteins B-100 and A-1 present in each admixture.

In any of the above assays it is preferred that the first-named, solid phase-bound, monoclonal paratopic molecules be those that are secreted by the hybridoma having ATCC accession number HB 8746, and that the third, solid phase-bound, paratopic molecules be those secreted by the hybridoma having the ATCC accession number HB 9200.

Another aspect of this invention constitutes a diagnostic system, typically in kit form. Such a system contains at least separate packages or containers, each of which has one of the before-discussed monoclonal paratopic molecules present in an amount sufficient to carry out one determination of the apo B-100 to apo A-I ratio. One of the pair of paratopic molecules that immunoreact with apo B-100 and one of the pair of paratopic molecules that immunoreact with apo A-I are operatively linked to an enzyme indicating means.

More preferably, the respective monoclonal paratopic molecules not linked to the respective indicating means are each separately bound to solid phase matrices to form separate solid phase supports. The surfaces of each of those supports has non-specific protein binding sites blocked. The solid matrices of those solid supports constitute the container or package for the respective paratopic molecules.

It is to be understood that although the paratopic molecules have been given numbers; i.e., first, second, third and fourth, as have the packages that contain them in diagnostic systems, those numbers are utilized for purposes of identification only and are not indicative of the order in which those paratopic molecules are admixed into a sample aliquot or the packaged contents are utilized. It is similarly to be understood that the before-described admixtures have been given numbers similar to those of the paratopic molecules that are admixed, but that those admixtures need not be formed in the order recited. Thus, for example, admixture of the before-described second aliquot with the third and fourth monoclonal paratopic molecules can occur in time prior to admixture of the before-described first aliquot with the first and second paratopic molecules. Similarly, as already noted, the first and second paratopic molecules can be admixed substantially simultaneously.

The present invention has several benefits and advantages. Salient among those benefits and advantages is the fact that by use of the assay methods described hereinafter a marker for abnormal lipid metabolism that is correlated to coronary artery disease (CAD) can be obtained that is accurate and reliable.

Another benefit and advantage of the present invention is that its assays can be carried out with the desired accuracy and precision in a relatively short period of time, e.g., within a period of about 1 hour, if that is desired.

Yet another benefit and advantage of the present invention is that whereas its method provides highly accurate and precise measurements for apo B-100, apo A-I and the ratio marker, those measurements are achieved without the use of radioactive elements and the detriments that the use of such elements normally provide.

Still further benefits and advantages of the present invention will be apparent to those skilled in the art from the detailed description of the invention that follows.

LDL was prepared from pooled plasma of 10 subjects (- - - - -) or from one normolipidemic subject (———). Plasma was obtained by plasmaphoresis of subjects following an approximately 12-hour fasting period.

Figure 2:
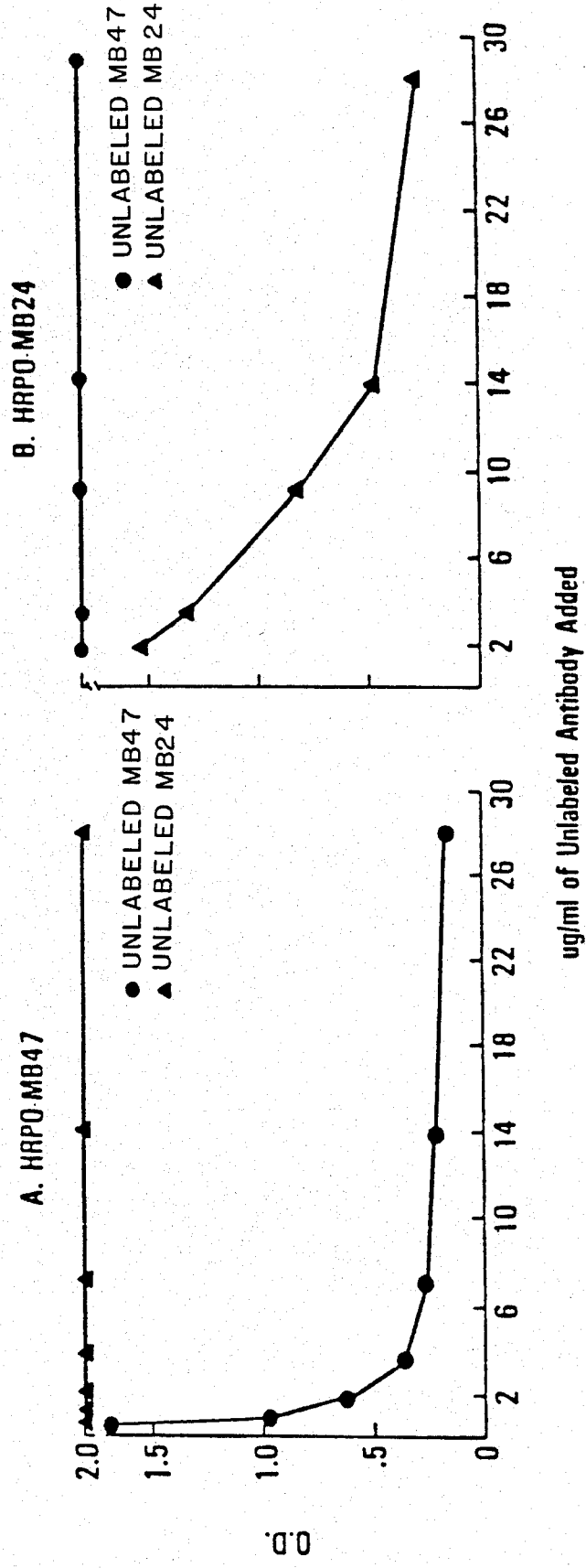

FIG. 2 contains two graphs. Graph A illustrates the ability of a known, constant amount of horseradish peroxidase-labeled MB47 (HRPO-MB47) molecules to immunoreact with solid phase-affixed reagent apo B-100 in the presence of increasing amounts of MB24 molecules. The ordinate is in relative optical density units, whereas the abscissa is in units of micrograms per milliliter (ug/ml) of unlabeled antibody protein added as competitor.

A constant amount (20 ug) of HRPO-coupled MB47 molecules was substantially simultaneously admixed with increasing amounts of unlabeled MB47 (●) or unlabeled MB24 (♦) molecules and solid phase-bound reagent apo B-100 (LDL). The admixtures were maintained for a time period of three hours at 25 degrees C. thereby allowing MB24 and MB47 paratopic molecules to immunologically react with the reagent apo B-100 and form a solid phase-bound immunoreactant. The amount of solid phase-bound labeled MB47 was then assayed as described in the Competitive ELISA portion of the Materials and Methods Section.

Graph A illustrates that the presence of increasing amounts of unlabeled MB47 paratopic molecules in the immunoreaction admixture correspondingly decreases the amount of labeled MB47 molecules bound as the solid phase immunoreactant. Thus, unlabeled MB47 competes with labeled MB47 for LDL.

Graph A also illustrates that increasing amounts of unlabeled MB24 molecules do not significantly decrease the amount of labeled MB47 bound as solid phase immunoreactant. Thus, unlabeled MB24 molecules do not compete with labeled MB47 molecules for binding to LDL.

Graph B illustrates that similar results are obtained using HRPO-labeled MB24 molecules and unlabeled MB47 molecules. MB47 and MB24 paratopic molecules therefore bind to different epitopes that are sufficiently separated on the surface of apo B-100 so as to allow binding of both molecules to a single apo B-100 molecule without sterically competing with and inhibiting the other's binding.

FIG. 3 contains two graphs labeled A and B. Graph A illustrates the ability of a known, constant amount (0.375 ug/ml) of horseradish peroxidase-labeled AI-10 molecules to immunoreact with solid phase-affixed reagent apo A-I in the presence of increasing amounts of unlabeled AI-10 (●) and AI-11 (♦) molecules. The ordinate is in optical density units, whereas the abscissa is in units of micrograms (ug) of unlabeled competing monoclonal antibodies added. This study is similar to that discussed for FIG. 2, and its details are provided in the Materials and Methods Section.

Graph A illustrates that increasing amounts of unlabeled AI-10 molecules in the immunoreaction admixture correspondingly decrease the amount of labeled AI-10 bound as the solid phase immunoreactant. Thus, unlabeled AI-10 competes with labeled AI-10 for apo A-I.

Graph A also illustrates that increasing amounts of unlabeled AI-11 molecules do not significantly decrease the amount of labeled AI-10 molecules bound as solid phase immunoreactant. Thus, unlabeled AI-11 molecules do not compete with labeled AI-10 molecules for binding to apolipoprotein A-I.

Graph B illustrates that similar results are obtained using HDL as antigen with a constant amount (0.375 ug/ml) of HRPO-labeled AI-10 molecules and unlabeled AI-11 molecules (■) and AI-10 molecules (♦). AI-10 and AI-11 molecules therefore bind to different epitopes that are sufficiently separated on the surface of apo A-I or apo A-I on HDL so as to permit binding of both monoclonal antibody molecules to a single apo A-I molecule without sterically competing with and inhibiting the other's binding.

DETAILED DESCRIPTION OF THE INVENTION

I. General Discussion

A. Definitions

The term "antibody" refers to a molecule that is a member of a family of glycosylated proteins called immunoglobulins that can specifically combine with an antigen. Such an antibody combines with its antigen by a specific immunologic binding interaction between the antigenic determinant of the antigen and the antibody combining site of the antibody.

An "antibody combining site" is that structural portion of an antibody molecule comprised of heavy and light chain variable and hypervariable regions that specifically binds antigen. Using the nomenclature of Jerne (1974) Ann. Immunol. (Inst. Pasteur), 125C:373-389, an antibody combining site is usually referred to herein as a "paratope".

Antibody combining site-containing (paratope-containing) polypeptide portions of antibodies are those portions of antibody molecules that contain the paratope and bind to an antigen, and include, for example, the Fab, Fab', F(ab')$_2$ and F(v) portions of the antibodies. Fab and F(ab')$_2$ portions of antibodies are prepared by the proteolytic reaction of papain and pepsin, respectively, on substantially intact antibodies by methods that are well known. See for example, U.S. Pat. No. 4,342,566 to Theofilopolous and Dixon. Fab' antibody portions are also well known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. Intact antibodies are preferred, and are utilized as illustrative of the monoclonal ligand molecules of this invention.

The word "antigen" has been used historically to designate an entity that is bound by an antibody, and also to designate the entity that induces the production of the antibody. More current usage limits the meaning of antigen to that entity bound by an antibody, whereas the word "immunogen" is used for the entity that induces antibody production. Where an entity discussed herein is both immunogenic and antigenic, it will generally be termed an antigen.

The phrase "antigenic determinant" refers to the actual structural portion of the antigen that is immunologically bound by an antibody combining site. The Jerne nomenclature redefines an antigenic determinant as an "epitope".

The term "biologically active" refers at least to the ability of a proteinaceous molecule to specifically bind antigen or specific antibody combining site, although other general or effector capability may be present in that molecule as well.

Biological activity of a paratopic molecule containing an antibody combining site is evidenced by the immunologic reaction of the paratope (antibody combining site) with its epitope (antigenic determinant) upon their admixture in an aqueous medium to form an immunoreactant, at least at physiological pH values and ionic strengths. Preferably, biological activity occurs under biological assay conditions; i.e., those conditions wherein a monoclonal paratopic molecule useful in this invention binds to the epitope (antigenic determinant) within a pH value range of about 5 to about 9, at ionic strengths such as that of distilled water to that of about one molar sodium chloride, and at temperatures of about 4 degrees C. to about 45 degrees C. The monoclonal paratopic molecules useful herein are all biologically active.

"ELISA" refers to an enzyme-linked immunosorbent assay that employs an antigen or antibody bound to a solid phase and an enzyme-antibody or enzyme-antigen conjugate to detect and quantify the amount of antigen or antibody present in a sample. A description of the ELISA technique is found in Chapter 22 of the 4th Edition of Basic and Clinical Immunology by D. P. Sites et al., published by Lange Medical Publications of Los Altos, Calif. in 1982 and in U.S. Pat. Nos. 3,654,090; 3,850,752; and 4,016,043, which are incorporated herein by reference.

"Enzyme" refers to a protein capable of accelerating or producing by catalytic action some change in a substrate for which it is often specific.

"Immunoreactant" as used herein refers to the product of an immunological reaction; i.e., that entity produced when an antigen is immunologically bound by an antibody or a molecule containing a paratope. An immunoreactant is therefore a specific type of complex formed between molecules.

The terms "indicating means", "enzyme indicating means" or "label" are interchangeably used herein in various grammatical forms to refer to enzymes that are directly involved in the production of a detectable signal to indicate their presence. Paratopic molecules when linked to enzyme labels are also sometimes referred to herein as being enzyme-linked paratopic molecules.

The term "whole antibody" is used herein to distinguish a complete, intact molecule secreted by a cell from other, smaller, molecules that also contain the paratope necessary for biological activity in an immunoreaction with an epitope.

The paratopic molecules useful in the present invention are monoclonal paratopic molecules. A "monoclonal antibody" (Mab) is a antibody produced by clones of a hybridoma that secretes but one kind of antibody molecule, and a monoclonal paratopic molecule is a monoclonal antibody or paratope-containing polypeptide portion thereof, as is discussed below. The hybridoma cell is fused from an antibody-producing cell and a myeloma or other self-perpetuating cell line. Such antibodies were first described by Kohler and Milstein, Nature, 256, 495–497 (1975), which description is incorporated herein by reference.

The terms "monoclonal paratopic molecule" and "paratopic molecule" alone are used interchangeably and collectively herein to refer to the genus of molecules that contain a combining site of a monoclonal antibody, and include a whole monoclonal antibody, a substantially whole monoclonal antibody and an antibody binding site-containing portion of a monoclonal antibody. The whole monoclonal antibodies designated MB47, MB24, AI-10 and AI-11 are paratopic molecules of this invention as are portions of those whole antibodies that include the paratope. The terms "monoclonal paratopic molecule" or "paratopic molecule" are used alone herein when a generic biolgically active molecule containing the paratope of the above monoclonal antibodies is intended. The terms MB47, MB24, AI-10 and AI-11 with and without the words "paratopic molecule" are used where the specific whole antibodies produced by hybridomas ATCC HB 8742, HB 8746, HB 9200 or HB 9201 are intended.

The words "secrete" and "produce" are often used interchangeably in the art as to cells from which antibody molecules are obtained. Cells that produce antibodies may, however, not secrete those molecules into their environment. The hybridoma cells of interest herein secrete monoclonal antibodies into their environment. Nevertheless, such cells are sometimes referred to herein as "antibody-producing" cells, and their antibodies are sometimes referred to as being "produced" in keeping with the phrase utilized in the art. Paratope-containing polypeptide portions of the above antibodies are similarly referred to herein as being "produced" or "secreted", although it is to be understood that such molecules are prepared from antibodies that are themselves "produced" or "secreted".

The terms "supernate" and "supernatant" are used interchangeably herein and refer to the in vitro liquid medium in which cells are cultured. Monoclonal antibodies produced by the hybridoma cultures of interest herein are secreted into their culture medium environment. Therefore the culture medium supernate for those cells is one preferred source of the monoclonal paratopic molecule and is readily obtainable free from hybridoma cells by well known techniques. Exemplary of such techniques is low speed centrifugation to sediment cells out of the liquid medium. Monoclonal paratopic molecules can alternatively be obtained from ascites tumor fluid (ascites fluid) of laboratory animals into which the hybridoma tissue was introduced. Both methods are described hereinafter.

The phrase "substantially simultaneously" as used herein in relation to the admixture of three or more antigen and paratopic molecule components to form an immunoreaction admixture means that all of the components are present and admixed in a single admixture within about 15 minutes of each other, and preferably within about 5 minutes of the admixture of any two of the components.

The phrase "substantially all" as used herein in relation to the immunoreaction of a paratopic molecule and its antigen either apolipoprotein B-100 as LDL or apolipoprotein A-I as HDL to form an immunoreactant means that the paratopic molecule immunoreacts with at least about 90 percent of the antigen present in solution to form the immunoreactant when the paratopic molecule is present in excess. In preferred practice, the paratopic molecule forms an immunoreactant with greater than 95 percent of the antigenic molecule present when that paratopic molecule is present also in excess.

B. Hybridomas and Monoclonal Paratopic Molecules

The present invention utilizes two pairs of two paratopic molecules that are secreted by four hybridomas. One pair of paratopic molecules immunoreact with apolipoprotein B-100. The other pair immunoreact with apolipoprotein A-I.

The hybridomas that secrete paratopic molecules that immunoreact with apo B-100 bear the laboratory designations HL130C2.3C5 and V82A6.1G4, and the whole monoclonal paratopic molecules secreted by those hybridomas are usually referred to herein as MB47 and MB24, respectively. Each of the paratopic molecules secreted by those hybridomas immunoreacts with more than about 90 percent of $^{125}$I-LDL, and with a distinct and separate conserved antigenic determinant on apo B-100. As is seen by examination of Graphs A and B of FIG. 2, MB47 and MB24 paratopic molecules both bind to apo B-100, each doing so without substantially inhibiting the immunoreaction of the other. As pointed out in Young et al. (1986) Clin. Chem., 32/8:1484–1490, MB47 reacts only with apo B-100, whereas MB24 immunoreacts with apo B-100 as well as cross-reacting with apo B-48, and also with apo B-26, a fragment of apo B-100 as is discussed hereinafter.

The second pair of hybridomas bear the laboratory designations H91H4.2H8 and H103D8.1D11, and secrete paratopic molecules designated AI-10 and AI-11, respectively. Each of these paratopic molecules AI-10 and AI-11, immunoreacts with a conserved antigenic determinant on apo A-1 and immunoreacts with greater than about 90 percent of $^{125}$I-HDL particles in a solid phase ELISA. As is seen from examination of Graphs A and B of FIG. 3, both paratopic molecules AI-10 and AI-11 bind to apo A-I and HDL, but do not substantially interfere with each others' binding.

Each of the above four hybridomas was deposited with the American Type Culture Collection (ATCC) 12301 Park Lawn Drive, Rockville, Md., in accordance with the Budapest Treaty on the International Recognition of the Deposit of Microorganisms for the Purposes of Patent Procedure.

| Hybridoma | Paratopic Molecule Designation | ATCC Accession Number | Deposit Date |
|---|---|---|---|
| V82A6.1G4 | M24 | HB 8742 | 3/6/85 |
| HL130C2.3C5 | MB47 | HB 8746 | 3/6/85 |
| H91H4.2H8 | AI-10 | HB 9200 | 9/16/86 |
| H103D8.1D11 | AI-11 | HB 9201 | 9/16/86 |

The above deposits were made in compliance with the Budapest Treaty requirements that the duration of the deposit should be for 30 years from the date of deposit or for 5 years after the last request for the deposit at the depository or for the enforceable life of a U.S. patent that matures from this application, whichever is longer. The hybridomas will be replenished should they become non-viable at the depository, and will be made available to the public by the ATCC upon the issuance of a patent from this application.

Previously, Curtiss et al., (1982) J. Biol. Chem., 257:15,213–15,221, reported production and characterization of 11 apo B specific paratopic molecules, including those designated MB24 produced by hybridoma HB 8742. Hybridoma HB 8742 was obtained by fusing splenocytes of mice immunized with human VLDL with myeloma cells.

MB24 was shown to immunoreact with denatured apo B-100 present in VLDL and LDL as well as denatured apolipoprotein B-26 of LDL and an unidentified high molecular weight LDL protein in that paper. More recent work indicated that it bound apo B-48. MB24 was shown to immunoreact with 100 percent of presented native LDL antigen in a fluid phase RIA in Tsao et al. (1982) J. Biol. Chem. 15,222–15,228.

The IgG fraction of MB24-containing ascites fluid generated from intraperitoneal growth of HB 8742 was characterized by isoelectric focusing (IEF). As noted in Curtiss et al., (1982) J. Biol. Chem., 257:15,213–15,221, the fusion was performed using P3×63Ag8 myeloma cells that secrete an IgG$_1$k immunoglobulin (myeloma protein). Therefore, upon IEF, HB 8742 ascites fluid demonstrated a unique pattern of multiple protein bands representing randomly mixed heavy and light chain-containing immunoglobulin molecules in addition to the P3×63Ag8 myeloma IgG$_1$k antibody and paratopic molecules MB24.

Hybridoma HB 8746 produces MB47 paratopic molecules and was formed by fusing splenocytes of mice immunized with LDL and P3×63Ag8.653.1 myeloma cells. That monoclonal antibody and hybridoma were reported by Young et al. (1986) Arteriosclerosis, 6:178–188. That variety of the parent myeloma cell line utilized to prepare the hybridoma does not secrete a myeloma protein. IEF of HB 8746 ascites fluid reveals a unique pattern of protein bands representing the IgG2a heavy and kappa light chains of MB47.

Thus, the above hybridomas can be characterized in part by the IEF pattern of the paratopic molecules they secrete. Whereas the hybridoma HB 8742 produces more than one type of paratopic molecule, the paratopic molecules useful in this invention can be easily identified and isolated by their individual abilities to immunoreact with epitope (antigenic determinants) on apo B-100.

The antigenic specificities of MB24 and MB47 were examined by assaying their individual abilities to immunoreact with apoproteins obtained from chylomicrons, VLDL, LDL, and HDL in various assays. The data so obtained indicated that MB47 and MB24 immunoreact with apo B-100 obtained from LDL, VLDL and IDL, but not with apo B-48 from VLDL or chylomicrons, and not with HDL. Fab fragments of MB47 and MB24 also bind to LDL in solid phase RIA.

Previous studies have demonstrated antigenic heterogeneity in apo B-100. That is, some apo B-100 epitopes are not expressed by all LDL particles. Thus, admixture with an excess of certain monoclonal antibodies in a fluid phase RIA does not result in immunological binding of all radiolabeled LDL $^{125}$I-LDL) particles.

To determine whether the epitope recognized by MB47 molecules was uniformly expressed by all LDL, the ability of MB47 to immunologically bind to $^{125}$I-LDL in a fluid phase RIA was studied. LDL isolated from pooled plasma of 10 normal subjects and from a single normal subject were radiolabeled as described hereinbelow and were admixed with biologically active MB47 molecules to form an immunoreaction admixture. The admixture was maintained under biological assay conditions for a predetermined time period sufficient for the MB47 molecules to immunologically bind to apo B-100 in each sample and form an immunoreaction product (immunoreactant).

Figure 1:
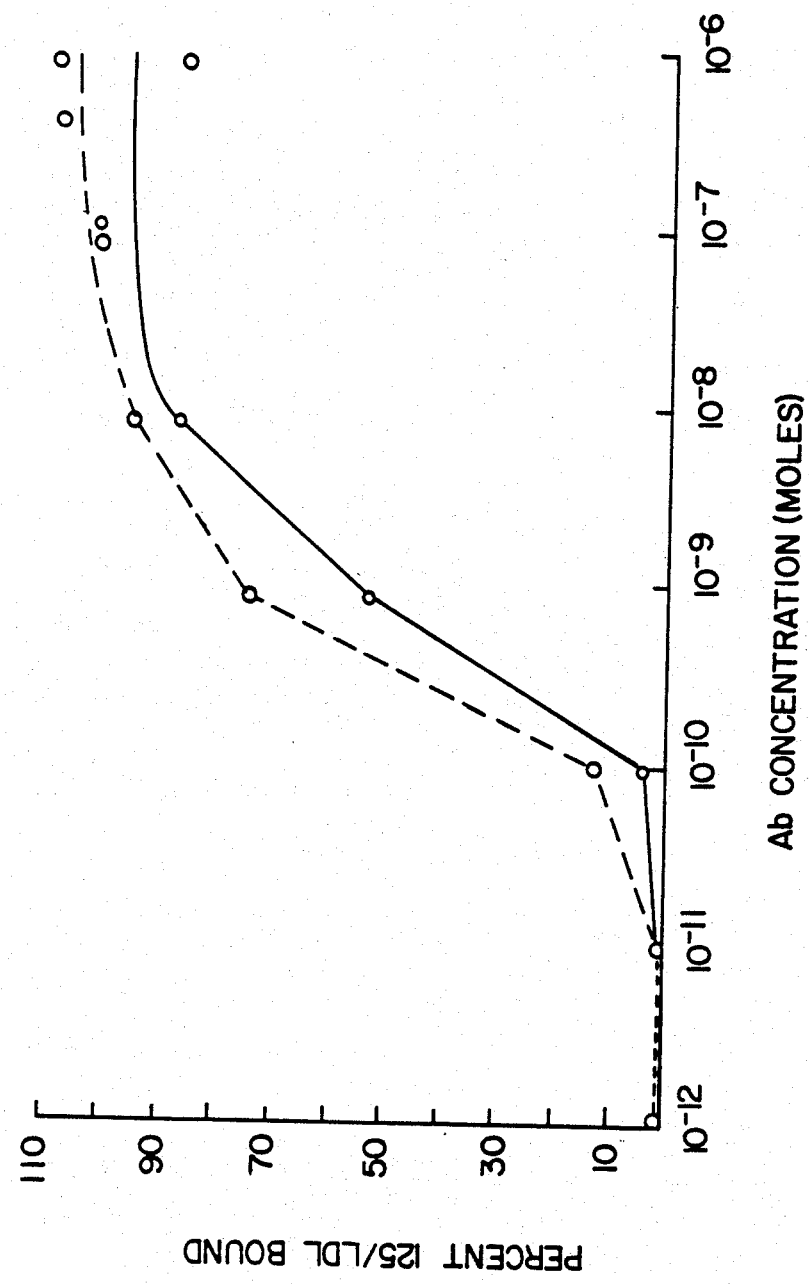
FIG. 1 is a graph showing the percentage of $^{125}$I-labeled LDL particles bound (ordinate) by increasing molar concentrations of monoclonal antibody MB47 [abscissa; Ab Concentration (MB47)] in a fluid phase radioimmunoassay (RIA).

The maximal amount of $^{125}$I-LDL bound by an excess of the MB47 paratopic molecules was assayed by precipitation of all receptor molecules with IgSORB (The Enzyme Co., Boston, Mass.) and quantitation of $^{125}$I-LDL associated counts in the precipitate in a gamma counter. The results, expressed as a percentage of $^{125}$I-LDL precipitated by trichloracetic acid (TCA) and shown in FIG. 1, demonstrate that essentially all $^{125}$I-LDL was bound by antibody, indicating that the epitope recognized and bound by MB47 is expressed by all LDL particles.

For the assay method of this invention the first and second monoclonal paratopic molecules must bind to different epitopes of the apo B-100 molecule, and those epitopes must be sufficiently separated such that the binding of one paratopic molecule does not sterically inhibit the binding of the other paratopic molecule. The capacity of MB47 and MB24 to competitively inhibit the binding of each other to solid phase-affixed reagent apo B-100 was therefore examined.

The results of that study, shown in FIG. 2, indicate that a 70-fold excess of unlabeled MB24 did not significantly inhibit peroxidase-labeled MB47 from binding to reagent apo B-100. Similarly, a 70-fold excess of unlabeled MB47 did not significantly inhibit peroxidase-labeled MB24 from binding to reagent apo B-100. Thus, MB24 and MB47 bind to different epitopes on apo B-100 and those epitopes are sufficiently separated such that MB24 and MB47 as intact antibodies do not inhibit the binding of each other to a single apo B-100 molecule.

The hybridomas producing monoclonal paratopic molecules AI-10 and AI-11 were prepared from two separate fusions of mouse splenocytes with cells of mouse myeloma line P3×63Ag8.653. Human HDL was used as the immunogen. AI-10 moecules are of the IgG2a class, whereas AI-11 molecules are of the IgG1 class.

As can be seen from an examination of FIG. 3, both AI-10 and AI-11 immunoreact with apo A-I. The data of FIG. 3 further illustrate that the immunoreaction of either of AI-10 or AI-11 with apo A-I or with HDL does not interfere with the immunoreaction of the other with that antigen.

Binding studies using $^{125}$I-HDL and $^{125}$I-apo A-I were carried out using RIA techniques as described generally in Curtiss et al. (1985) *J. Biol. Chem.* 260:2982-2993. The results of those studies are shown in Table 1, below, as percentages of total trichloracetic acid (TCA)-precipitable radioactivity.

TABLE 1

| Paratopic Molecules[1] | Immunoreactivities of AI-10 and AI-11 | |
|---|---|---|
| | Maximal Binding of Antigen (%) | |
| | $^{125}$I-HDL[2] | $^{125}$I-Apo A-I[2] |
| AI-10 as: | | |
| Supernatant | 29.2 | 90.3 |
| Ascites | 92.6 | — |
| FPLC Ascites | 86.0 | 70.2 |
| AI-11 as: | | |
| Supernatant | 88.6 | 42.0 |
| Ascites | 100.0 | 49.0 |
| FPLC Ascites | 93.0 | 60.4 |

[1]Fluid phase paratopic molecules were used from hybridoma cell culture supernatant (Supernatant), mouse ascites fluid (Ascites), and fast protein liquid chromatography-purified ascites fluid (FPLC Ascites).
[2]Percentage of TCA-precipitable radioactivity.

The data of Table I illustrate the relatively high binding of whole AI-10 and AI-11 to radiolabeled HDL in the fluid phase assay utilized. Those data also reflect the relative instability of and resulting low binding to apo A-I itself. That relative instability of apolipoprotein A-I has necessitated the use of HDL as a secondary standard in the apo A-I assay as is discussed further hereinafter. The above data also illustrate a relatively lower binding of AI-11 to apo A-I than to HDL particles. Nevertheless, a comparison of data obtained utilizing the ELISA method for apo A-I with data obtained by other, more laborious techniques indicates that the ELISA method quantitatively detects substantially all of apolipoprotein A-I (HDL) present in samples assayed.

C. Abnormal Lipid Metabolism Marker

As previously noted, several studies have shown a correlation between high levels of LDL with relatively low levels of HDL and abnormal lipid metabolism leading to and thus an increased risk of CAD. Abnormal lipid metabolism is also of import for following the disease course in persons diagnosed clinically as having CAD. However, those studies have not provided a marker and a clear cut dividing line between those persons who are normal and those exhibiting abnormal lipid metabolism.

Thus, for example, Kottke et al. (1986) *Mayo Clin. Proc.* 61:313-320, measured the serum levels of apolipoproteins A-I, A-II and B, HDL cholesterol, triglycerides and age as variables in males, and found that the use of all six of those variables were required to accurately discriminate CAD patients from asymptomatic controls. Those workers utilized radioimmunoassays for their determinations of apolipoproteins.

Polyclonal antibodies, an antibody-sample maintenance time of 16 hours, and an unmasking, detergent treatment were reportedly utilized for the RIA measurement of apo A-I values by Kottke et al. A monoclonal antibody was reportedly utilized for the RIA measurement of apo B. Kottke et al. reported mean serum apo A-I values for normals and CAD patients that did not overlap within one standard deviation. Their values for mean serum apo B between those two groups overlapped within one standard deviation.

Those workers did not report a ratio of their values for apo B and apo A-I.

In addition, Bentzen et al. (1982) *Clin. Chem.* 28:1951–1956, reported using a ratio of beta-lipoprotein cholesterol (LDL-cholesterol) to alpha-lipoprotein cholesterol (HDL-cholesterol) as a marker to indicate a patient's risk of stroke or coronary heart disease as compared to using the value of HDL cholesterol alone. Of course, lipoprotein cholesterol values are different from LDL and apo B-100 or HDL and apo A-I, and the method used by those workers, which was based upon affinity chromatography over hepanin-agerose, differs greatly from the method utilized herein.

II. The Improved Method

In accordance with the present invention, the ratio of apolipoprotein B-100 to apolipoprotein A-I in a liquid blood sample is utilized as a marker for an abnormal lipid metabolism in persons who have not been identified as having the disease, as well as in diagnosed CAD patients. Once CAD or abnormal lipid metabolism is identified by the assay method, the person is typically treated by conventional therapy such as by excercise, diet or specific drugs as is well known.

A liquid blood sample is utilized in this method. The sample can be either serum or plasma, as results obtained using both have been found to be statistically indistinguishable. Indeed, some results reported hereinafter using the method were obtained using averaged values obtained from assays of both serum and plasma. Regardless of whether serum or plasma is used, the liquid blood sample is preferably obtained from persons who have fasted for at least about twelve hours as is known in the art. Such a blood sample is referred to as a "fasting" sample.

It was surprising that accurate and precise results could be obtained utilizing the present ELISA methods with a liquid blood sample such as plasma or serum because those sample materials contain proteins, lipids and other compounds that could be expected to interfere with the assay. See, for example, Maggio, *Enzyme-Immunoassay*, CRC Press, Inc. Boca Raton, Fla., 1980, page 65.

In the improved method of this invention, the blood sample is divided into at least two aliquots. One sample aliquot is utilized for the apo B-100 determination and the other for the apo A-I determination.

Starting with the analysis for apolipoprotein B-100, a first solid-liquid phase admixture is formed by admixing a predetermined amount of a first liquid blood sample aliquot with a solid support that consists essentially of a solid matrix having solid phase-bound first monoclonal paratopic molecules that immunoreact with apo B-100. Those solid phase-bound first monoclonal paratopic molecules are present in excess over the amount of apo B-100 expected in the sample, and are secreted by one of the hybridomas having ATCC accession numbers HB 8742 or HB 8746. Non-specific protein binding sites on the surface of that solid suport are blocked prior to that admixture.

That first solid-liquid phase admixture is maintained under biological assay conditions for a predetermined period of time that is sufficient for the first paratopic molecules to immunoreact with apolipoprotein B-100 present in the sample aliquot and form a solid phase-bound immunoreactant that contains substantially all apolipoprotein B-100 present in the sample aliquot.

The apo B-100 of the first sample aliquot is also admixed with liquid phase second monoclonal paratopic molecules that immunoreact with apolipoprotein B-100 to form a second admixture. Those second monoclonal paratopic molecules are secreted by one of the hybridomas having ATCC accession numbers HB 8742 or HB 8746 but are not utilized in the first-named admixture. Those second paratopic molecules are also operatively linked to an enzyme indicating means.

The second admixture is maintained under biological assay conditions for a predetermined period of time sufficient for the second, enzyme-linked paratopic molecules to form an immunoreactant that contains substantially all apolipoprotein B-100 in the sample aliquot.

The solid and liquid phases that result from admixture of both paratopic molecules and formation of immunoreactants between both paratopic molecules and apo B-100 are separated as by rinsing, and the amount of indicating means-linked apolipoprotein B-100-containing immunoreactant present in the separated solid phase is determined. Because each of the two monoclonal paratopic molecules immunoreact with substantially all of the apo B-100 present in the sample aliquot, and because at least one of the paratopic molecules immunoreacts with a non-cross-reactive, conserved epitope on apo B-100, determination of the amount of enzyme-linked apo B-100 in the immunoreactant provides a determination of the amount of apo B-100 present in the sample aliquot. The amount of apolipoprotein B-100 per unit volume of sample can readily be calculated by knowledge of the volume of the originally utilized, predetermined amount, of liquid blood sample aliquot.

The amount of apolipoprotein A-I is determined using a second, predetermined amount of liquid blood sample aliquot. Contrary to procedures utilized by others, the second liquid blood sample aliquot is free from an unmasking treatment as is usual for measurement of apo A-I.

Steps analogous to those described before for apolipoprotein B-100 are followed except that third and fourth monoclonal paratopic molecules secreted by one of the hybridomas having ATCC accession numbers HB 9200 or HB 9201 are utilized for the second blood sample aliquot. In keeping with the analogy of those previously described steps, solid phase-bound third monoclonal paratopic molecules are admixed with the second blood sample to form a third solid-liquid phase admixture, and that third solid-liquid phase admixture is maintained as described before to form a solid phase-bound immunoreactant that contains substantially all apolipoprotein A-I present in the sample aliquot.

The apolipoprotein A-I in the second sample aliquot is also admixed with liquid phase fourth monoclonal paratopic molecules discussed before that are not those bound to the solid matrix and are operatively linked to an enzyme indicating means to form a fourth admixture. That fourth admixture is maintained as described before for a period of time sufficient for the fourth, enzyme-linked monoclonal paratopic molecules to form an immunoreactant with substantially all apolipoprotein A-I present in the sample aliquot.

The solid and liquid phases that result from the admixing and maintaining steps are separated, and the amount of enzyme indicating means-linked apolipoprotein A-I-containing immunoreactant present in the separated solid phase is determined, thereby providing a determination of the amount of apolipoprotein A-I in the sample aliquot and per unit volume, as discussed before.

The assays for apo B-100 and apo A-I discussed before can each be carried out with each of the admixing and maintaining steps in each assay being carried out sequentially, or the two admixing steps in each assay can be carried out substantially simultaneously with the two maintaining steps in each assay being carried out together.

When the steps are carried out sequentially, it is preferred that the solid phase-bound monoclonal paratopic molecules be admixed and the formed admixture maintained prior to admixture of the enzyme indicating means-linked paratopic molecules and maintenance of that resulting admixture. When the preferred, sequential steps are followed, it is further preferred that the solid and liquid phases formed be separated, and the solid phase rinsed to help assure that separation, before the admixture of the liquid enzyme indicating means-linked paratopic molecules to the separated solid phase and maintenance of that admixture.

It is also noted that the enzyme indicating means-linked paratopic molecules can be the first admixed with the appropriate sample aliquot. When this mode of carrying out the method is utilized there is no separating of phases prior to admixture of the solid phase-bound monoclonal paratopic molecules.

Most preferably for the assay of both apolipoprotein B-100 and apolipoprotein A-I, the solid phase-bound monoclonal paratopic molecules, blood sample aliquot and enzyme indicating means-linked paratopic molecules are separately admixed substantially simultaneously, and each of the resulting solid-liquid phase admixtures is maintained together. Thus, each admixture is maintained for a period of time sufficient for the two separate solid phase-bound monoclonal paratopic molecules to form solid phase-bound immunoreactants with substantially all of the apo B-100 and apo A-I, respectively, and for the two phase liquid enzyme indicating means-linked paratopic molecules to also immunoreact with substantially all of the apo B-100 and apo A-I, respectively, in the respective sample aliquots. The immunoreactants so formed are referred to as solid phase-bound sandwich immunoreactants. A liquid phase also is present.

Similar results are obtained using either of the monoclonal paratopic molecules of the two sets of paratopic molecules as the solid phase-bound paratopic molecules in the respective assays. However, most of the work discussed herein was carried out using the molecules secreted by the hybridoma having ATCC accession No. HB 8746 (MB47) bound to the solid matrix when apolipoprotein B-100 was assayed, and the molecules secreted by the hybridoma having ATCC accession No. HB 9200 (AI-10) bound to the solid phase matrix when apolipoprotein A-I was assayed. In addition, it is particularly preferred to use MB47 as the solid phase-bound paratopic molecules since those molecules do not immunoreact with apo B-48 as can be present in chylomicrons of non-fasting blood samples or in persons with abnormally high chylomicron levels. Thus, the binding of chylomicrons to the solid support, because of their large size, may interfere with the additional binding of substantially all of the apo B-100 (LDL), even where the amount of solid phase-bound paratopic molecules is in excess of the apo B-100 in the assayed sample.

Exemplary solid matrices useful in the above methods are well known in the art and include a solid matrix such as 96-well microtiter plates sold under the designation Falcon Microtest III Flexible Assay Plates (Falcon Plastics, Oxnard, Calif.) or a microtiter strip containing twelve wells in a row, such as those strips sold under the designation Immulon I and II (Dynatech, Alexandria, Va.). The microtiter strip or plate is made of a clear plastic material, preferably polyvinylchloride or polystyrene. Alternative solid matrices for use in a before-described method of this invention include polystyrene beads, about 1 micron to about 5 millimeters in diameter, available from Abbott Laboratories, North Chicago, Ill.; polystyrene tubes, sticks or paddles of any convenient size; and polystyrene latex whose polystyrene particles are of a size of about 1 micron and can be centrifugally separated from the remainder of the latex.

The solid matrix can also be made of a variety of materials such as cross-linked dextran, e.g. Sephadex G-25, -50, - 100, - 200 and the like available from Pharmacia Fine Chemicals of Piscataway, N.J., agarose and cross-linked agarose, e.g. Sepharose 6B, CL6B, 4B, CL46 and the like also available from Pharmacia Fine Chemicals.

The enzyme indicating means is linked directly to a paratopic molecule useful in this invention to form a conjugate. It is to be understood that useful enzyme molecules linked to a paratopic molecule are operatively linked. Thus, the function of the enzyme is not substantially impaired by the linkage or paratopic molecule, nor is the function of the monoclonal paratopic molecule to which the enzyme is linked substantially impaired by that linkage or the presence of the enzyme.

The enzyme indicating means is a biologically active enzyme such as horseradish peroxidase (HRPO) or glucose oxidase, or the like. As is well known, where the indicating means is an enzyme such as HRPO or glucose oxidase, additional reagents are required to visualize the fact that a antibody-antigen complex has formed. Such additional reagents for HRPO include hydrogen peroxide and an oxidation dye precursor such as diaminobenzidine. Additional reagents useful with glucose oxidase include glucose and 2,2'azino-di-(3-ethylbenzthiazoline-6-sulfonic acid) (ABTS).

Techniques for operatively linking an enzyme to a paratopic molecule to form a conjugate are well known in the art. Exemplary techniques are discussed in Maggio, *Enzyme-Immunoassay,* Chapter 4 by Kabakoff, CRC Press, Boca Raton, Fla. (1980), pages 71–104.

The monoclonal paratopic molecules can be utilized as obtained from hybridoma supernatants or as ascites. However, it is preferred that purified paratopic molecules be utilized.

Several means for purification of paratopic molecules are well known in the art and typically utilize chromatographic techniques. Fast protein liquid chromatography (FPLC) is the purification technique of choice herein.

The enzyme-linked paratopic molecule conjugates are provided to the admixtures in the fluid phase. Those molecules are typically dissolved in an aqueous composition. Typical compositions contain buffer salts as is the case of the exemplary purified monoclonal antibody-containing compositions used herein that include phosphate-buffered saline (PBS) as a diluent. Diluted ascites fluid also is useful.

As noted before, non-specific protein binding sites on the surface of the solid phase support are blocked. Thus, the solid phase-bound paratopic molecules are bound as by adsorption or other well known means of affixation to the solid matrix. Thereafter, an aqueous solution of a protein free from interference with the assay such as bovine, horse or other serum albumin that also is free from contamination with human apo B-100 or apo A-I is admixed with the solid phase to adsorb the admixed protein onto the surface of the paratopic molecule-containing solid support at protein binding sites on the surface that are not occupied by the monoclonal paratopic molecule.

A typical aqueous protein solution contains about 3 to about 10 weight percent bovine serum albumin in PBS at a pH value of 7.1–7.5. The aqueous protein solution-solid support admixture is typically maintained for a time period of at least one hour at 37 degrees C., and the resulting solid phase is thereafter rinsed free of unbound protein.

The liquid blood sample can be plasma or serum, as already noted. That sample for apo A-I is preferably diluted at about 1:2500 to about 1:20,000, and more preferably at about 1:5000, prior to use to obtain linear results in the assays specifically described hereinafter. For apo B-100, the sample is preferably diluted at about 1:500 to about 1:5000, and more preferably at about 1:1000. The use of lesser dilution can provide too much of the apolipoprotein antigen to the admixture and impair the linearity of the assay results as well as lower or abolish the solid phase-bound paratopic molecule excess over the admixed antigen. Use of greater than about a 1:20,000 dilution tends to decrease precision.

The maintenance times utilized can vary widely with little variance in result so long as a minimum time of about 30 minutes at ambient room temperature (about 20–25 degrees C.) is utilized. Where it is desired to use a minimum 30-minute maintenance time, it is preferred that the maintained admixture be agitated during that time period to assure substantially complete immunoreaction between the apolipoprotein antigen and monoclonal paratopic molecules. Where longer maintenance times such as one hour or more at room temperature are utilized, agitation is not required. The desired agitation can be readily supplied by means of a gyro-shaker operated at about 100 rpm. Each of the assays used in the method is capable of being carried out using paratopic molecule-sample admixture maintenance times of about 30 minutes to about 60 minutes at ambient room temperatures.

The amount of apolipoprotein antigen present in the assayed immunoreactant is determined by admixture of the separated enzyme-linked apolipoprotein-containing solid phase with a predetermined amount of visualizing reagent or reagents. Where HRPO is utilized as the enzyme indicating means, visualizing reagents such as hydrogen peroxide and an oxidative dye precursor such as o-phenylenediamine (OPD) present in an aqueous medium are admixed with the separated solid phase-bound immunoreactant. The admixture so formed is maintained under biological assay conditions for a predetermined time such as at least about 30 minutes at ambient temperature for color to develop. Color development is thereafter stopped by admixture of a stopping reagent such as sulfuric acid. The optical density of the composition is thereafter read, compared to a standard curve value, and the amount of apolipoprotein is determined, as is well known.

Thus, once the solid suport and liquid blood sample are prepared, each assay can be carried out at ambient room temperature in a time period of about one hour; i.e., a 30-minute maintenance time with agitation for admixtures formed from both paratopic molecules and the sample aliquot, and another 30-minute maintenance time for color development. Indeed, one need not prepare the solid support just prior to each use, but rather, such supports as are described herein can be prepared and stored damp and covered under usual refrigeration conditions for a period of at laast one month prior to use.

Each of the apo B-100 and apo A-I assays utilizes a standard against which the optical density values obtained in the ELISAs are compared to calculate the concentrations of those two apolipoproteins. Both assays utilize secondary standards. That is, rather than utilizing apo B-100 and apo A-I as standards, the assays utilize human LDL and HDL, respectively, as the standards. The secondary standards are utilized because of the relative instability on storage of the primary apolipoproteins. Kottke and co-workers also noted degradation of purified apo A-I used as a primary standard, and utilized a secondary standard in their RIA with polyclonal serum for apo A-I. Au et al. (1986) Clin Chem. 32:1394–1397.

The secondary standards are typically provided as lyophilized LDL and HDL from pooled human fasting plasma, and are reconstituted prior to use. Each of the standards is itself standardized against primary standards of apo B-100 as LDL and apo A-I as HDL. Exemplary procedures are illustrated for apolipoprotein B-100 (LDL) and apolipoprotein A-I (HDL) in the Materials and Methods Section.

III. DIAGNOSTIC SYSTEMS

The present invention also contemplates a diagnostic system, typically in kit form, that can be utilized in carrying out the before-described methods. The system includes, in separate containers, at least the before-described monoclonal paratopic molecules MB47 and MB24 that immunoreact with apo B-100, and AI-10 and AI-11 that immunoreact with apo A-I. One of the paratopic molecules of each pair; i.e., one of MB47 and MB24, and one of AI-10 and AI-11, are linked to an enzyme indicating means as conjugates. The packages contain an amount of each of those paratopic molecules sufficient to carry out at least one assay for the marker of abnormal lipid metabolism.

More preferably, the system contains two solid supports each of which consists essentially of a solid matrix having bound monoclonal paratopic molecules that immunoreact with either apo B-100 or apo A-I, respectively, and whose surface non-specific protein binding sites are blocked, as well as two separately packaged enzyme-linked monoclonal paratopic molecule conjugates that immunoreact with apo B-100 and apo A-I, respectively. The same four paratopic molecules are utilized as are discussed hereinabove.

The solid phase matrices of the above diagnostic system can be any of the solid phase matrices discussed before, although both matrices are preferably of the same type. Microtiter wells such as those of the before-described 12-well strips and 96-well plates are particularly preferred. Non-specific binding sites on the solid supports are blocked as previously discussed.

The solid matrix constitutes a container for the bound monoclonal paratopic molecules of this embodiment. Typical containers for the enzyme-linked monoclonal paratopic molecules are vials or bottles made from glass or a plastic such as polyethylene or polypropylene.

Using a microtiter plate as an exemplary solid matrix, and, whole monoclonal antibodies MB47 and AI-10 as the solid phase-bound monoclonal paratopic molecules, serum as the liquid blood sample, and, whole monoclonal antibodies MB24 and AI-11 linked to HRPO, an exemplary more preferred diagnostic system in kit form includes the following:

(a) a solid support that consists essentially of a microtiter plate having monoclonal antibody MB47 bound thereto in an amount sufficient to carry out an assay of a serum sample aliquot for the amount of apolipoprotein B-100 present therein, and whose surface non-specific protein binding sites are blocked;

(b) a solid support that consists essentially of a microtiter plate having monoclonal antibody AI-10 bound thereto in an amount sufficient to carry out an assay of a serum sample aliquot for the amount of apolipoprotein A-I present therein, and whose surface non-specific protein binding sites are blocked;

(c) a separate package that contains an aqueous solution containing monoclonal antibody MB24 linked to HRPO that is present in an amount sufficient to carry out an assay of a serum sample aliquot for the amount of apo B-100 present therein; and (d) a separate package that contains an aqueous solution containing monoclonal antibody AI-11 linked to HRPO that is present in an amount sufficient to carry out an assay of a serum sample aliquot for the amount of apo A-I present therein.

Most preferably, a diagnostic system includes the above four components (a-d) and one or more of the following: (i) a supply of hydrogen peroxide of known concentration; (ii) a visualizing oxidative dye precursor such as OPD; (iii) a solution of a stopping agent such as 4N sulfuric acid to quench the color-forming reaction; (iv) one or more buffers in dry or liquid form for use in the assay; (v) materials for preparing standard reference curves; and (vi) instructions for carrying out the assays. Each of the immediately above-enumerated components is present in the diagnostic system in an amount sufficient to carry out at least one assay, and those components are separately packaged as is appropriate.

IV. RESULTS

The results obtained using the assay method described hereinbefore and in greater detail hereinafter in the Materials and Methods Section are discussed below. Wells of polystyrene 96-well microtiter plates were utilized as solid matrices. Whole monoclonal antibodies MB47 and AI-10 were utilized as the solid phase-bound first and third monoclonal paratopic molecules, in apolipoprotein B-100 and A-I assays, respectively. Non-specific protein binding sites on the solid support surfaces were blocked with BSA. HRPO-linked whole monoclonal antibodies MB24 and AI-11 were utilized as the second and fourth monoclonal paratopic molecules in apolipoprotein B-100 and A-I assays, respectively, with OPD as the visualizing oxidative dye precursor.

Assays for apo B-100 and apo A-I were carried out for 37 persons with no history of CAD. Those persons are referred to as "normals".

Values were obtained using diluted plasma and serum as the liquid blood samples. Those values were found to show no statistically significant differences between the two sample sources and were averaged for use.

A composite of the results for the "normals" is shown in Table 2, below, for the 23 men and 14 women separately, and as "combined" values.

TABLE 2

| Normal Apolipoprotein Levels | | |
|---|---|---|
| Males | Females | Combined |
| Apolipoprotein A-I[1] | | |
| n = 23 | n = 14 | n = 37 |
| mean = 143 | mean = 152 | mean = 147 |
| S.D. = 26.5 | S.D. = 10.7 | S.D. = 22.0 |
| S.D. Range = 116–170 | S.D. Range = 141–163 | S.D. Range 125 =–169 |
| Apolipoprotein B-100 | | |
| n = 23 | n = 14 | n = 37 |
| mean = 78.0 | mean = 77.5 | mean = 77.8 |
| S.D. = 17.6 | S.D. = 20.6 | S.D. = 18.8 |
| S.D. Range = 60.4–95.6 | S.D. Range = 56.9–98.1 | S.D. Range = 59.0–96.6 |
| Males[1] | Females[1] | Combined[1] |
| Ratio of Apolipoprotein B-100 to Apolipoprotein A-I | | |
| n = 23 | n = 14 | n = 37 |
| mean = 0.56 | mean = 0.51 | mean = 0.54 |
| S.D. = 0.16 | S.D. = 0.14 | S.D. = 0.15 |
| S.D. Range = 0.40–0.72 | S.D. Range = 0.37–0.65 | S.D. Range = 0.39–0.69 |

[1]"n" is the number of persons in each study. "mean" is the mean value obtained expressed in milligrams per deciliter for apo A-I and apo B-100, and as a unitless parameter for the ratio. "S.D." is the value of one standard deviation from the mean. "S.D. Range" is the breadth of one standard deviation on either side of the mean. Assays were carried out as described in the Materials and Methods Section.

Values were similarly obtained using the serum and plasma of 42 males who were clinically identified as having CAD. A composite of those values is shown in Table 3, below.

TABLE 3

| Male CAD Apolipoprotein Levels[1] |
|---|
| Apolipoprotein A-I |
| n = 42 |
| mean = 110 |
| S.D. = 28.8 |
| S.D. Range = 81.2–139 |
| Apolipoprotein B-100 |
| n = 42 |
| mean = 112 |
| S.D. = 27.8 |
| S.D. Range = 84.2–140 |
| Ratio of Apolipoprotein B-100 to Apoliprotein A-I |
| n = 42 |
| mean = 1.08 |
| S.D. = 0.38 |
| S.D. Range = 0.70–1.46 |

[1]See Table 2 footnote.

In reviewing the above data and comparing those data to the data provided in Kottke et al. (1986) *Mayo Clin. Proc.*, 61:313–320, several features stand out.

One feature is that the mean values for normal and CAD patients for apo A-I in the above assay are similar to those reported by Kottke et al. Similar standard deviations were obtained for both assay types.

This similarity of result was surprising for several reasons. First, the Kottke et al. workers used a detergent (Tween 20) unmasking treatment for their assays, whereas the present liquid blood samples were free of such treatments. Second, the Kottke et al. group utilized a radioimmunoassay, which is generally considered to be more accurate and precise than an ELISA as used herein. See Voller et al. (1976) *Bull. World Health Organ.*, 53:55–65. Third, polyclonal antibodies that are normally considered capable of improved immunoraction with the relatively heterogeneous apo A-I were used by Kottke et al., whereas monoclonal antibodies were used herein. Fourth, the Kottke et al. group utilized a maintenance time of 16 hours at room temperature for the immunoreaction of their polyclonal antibodies with apo A-I, whereas a time period of 30 minutes at room temperature was utilized herein.

Another feature is that whereas the mean values for apo B-100 for normal and CAD patients are slightly less in the present assays as compared to the respective mean values of Kottke et al., the standard deviations found in the present assays are quite a bit smaller than those reported by Kottke et al. Both Kottke et al. and the present inventors utilized monoclonal antibodies for their analyses, although Kottke et al. again utilized RIA as compared to the present ELISA.

Comparisons also were made using commercially available RID assays for apo B-100 along with the apo A-I assay described herein to obtain ratios of apo B-100 to apo A-I. Summaries of those results for the ratios in normal and CAD patients are shown in Table 4, below. Aliquots of one blood sample from each of the 20 normals and 40 CAD patients were used in this study to provide internal controls.

TABLE 4

Ratios of Apolipoprotein B-100 to Apolipoprotein A-I Obtained by Different Methods

| Present Invention[2] | RID I[2,3] | RID II[2,4] |
|---|---|---|
| Normals[1] | | |
| n = 20 | n = 20 | n = 20 |
| mean = 0.53 | mean = 0.74 | mean = 0.58 |
| S.D. = 0.12 | S.D. = 0.23 | S.D. = 0.17 |
| S.D. Range = 0.41–0.65 | S.D. Range = 0.51–0.97 | S.D. Range = 0.41–0.75 |
| CAD Patients[5] | | |
| n = 40 | n = 40 | n = 40 |
| mean = 1.07 | mean = 1.26 | mean = 1.01 |
| S.D. = 0.39 | S.D. = 0.40 | S.D. = 0.43 |
| S.D. Range = 0.68–1.46 | S.D. Range = 0.86–1.66 | S.D. Range = 0.58–1.44 |

[1]Values obtained from blood samples of both males and females.
[2]See Table 2 footnote.
[3]RID kit sold by Calbiochem-Behring of San Diego, CA used following package instructions with plasma.
[4]RID kit sold by Tago of Burlingame, CA used following package instructions with plasma.
[5]Values obtained from males with clinical CAD manifestations.

Examination of the data in the above Table shows that unacceptably large overlaps were obtained in the ratio, standard deviation ranges when marker values for normal persons and CAD patients were obtained using either of two commercially available RID kits for the apo B-100 assay as compared to use of the present apo B-100 assay in conjunction with the present apo A-I assay.

V. MATERIALS AND METHODS

A. Paratopic Molecule Preparation and Purification

1. Isolation of Anti-Apo A-I Immunoglobulin

Ascites fluids were obtained from 10 week old Balb/c mice, which had been primed with 0.3 ml of mineral oil and injected intraperitoneally with $3$–$50 \times 10^5$ hybridoma cells. The average time for development of ascites was 9 days. Following clarification by centrifugation at 15,000 xg for 15 hours at 23 degrees C., ascites fluids were pooled and stored frozen at $-20$ degrees C.

Isolated AI-10 and AI-11 antibodies were prepared by fast protein liquid chromatography (FPLC) using a Pharmacia Mono Q HR5/5 anion exchange column (Pharmacia Fine Chemicals, Piscataway, N.J.) using a 0–0.5M NaCl gradient in 10 mM Tris, pH 8.0. Purified Mabs were concentrated using an Amicon stirred ultrafiltration cell (Danvers, Mass.; PM 30 membrane) to a concentration of 1 milligram per milliliter (mg/ml), dialyzed into PBS (phosphate-buffered saline pH 7.2) and stored at $-70$ degrees C.

2. Isolation of Anti-Apo B-100 Immunoglobin

Ascites fluids containing anti-apo B-100 paratopic molecules useful herein were obtained from 10-week-old Balb/c mice, that had been primed with 0.3 ml of mineral oil and injected intraperintoneally with $3$–$50 \times 10^5$ hybridoma cells. The average time for development of ascites was 12 days. Following clarification by centrifugation at 15,000 xg for 1 hour at 4 degrees C., ascites fluids were pooled and stored frozen at $-20$ degrees C.

Isolated antibody MB47 was prepared by chromatography of the monoclonal hybridoma ascites fluids on a protein A-Sepharose 4B column (Pharmacia Fine Chemicals, Piscataway, N.J.). Antibody was eluted from the column with 0.1 molar (M) acetic acid.

Isolated paratopic molecules also were prepared by fast protein liquid chromatography (FPLC) of a monoclonal hybridoma ascites fluid on a Pharmacia Mono Q HR 5/5 anion exchange column in a Pharmacia FPLC System using a 0–0.5M NaCl gradient in 10 mM Tris, pH 8.0, and following the directions supplied with the column.

B. Characterization of Hybridoma Antibodies

The total gamma-globulin (Ig) content of each pool of ascites fluid was obtained by electrophoresis of 1–3 ml samples of cellulose acetate strips in 75 mM veronal buffer, at a pH value of 8.6 for 45 minutes at 200 millivolts (mV). The percentage of the total protein that was Ig was quantitated by densitometric scanning of the Ponceau S-stained gels, and total protein was determined by the modified Lowry methods as discussed before.

Murine Ig heavy and light chains for MB47 and MB24 were identified by double diffusion in 0.9 percent agarose. Ten microliters of an appropriate dilution of ascites fluid were reacted with an equal volume of appropriately diluted rabbit anti-murine heavy and light chain-specific antisera (Litton Bionetics, Inc. Charleston, S.C.). Following diffusion for about 15 hours at 20 degrees C. and washing, precipitin lines were identified by staining with 0.5 percent Coomassie brilliant blue R-250.

The subclasses of monoclonal antibodies AI-10 and AI-11 were identified using commercial radial immunodiffusion kits available from Meloy Laboratories, Inc. (Springfield, Va.) or Tago, Inc. (Burlingame, Calif.). Ascites fluid was delivered into a well cut into an agarose gel that contained either anti-IgG1, anti-IgG2a, anti-IgG2b, or anti-IgM. A visible precipitin ring formed with the antibodies of the identified class after a predetermined, specific time under controlled conditions. The diameter of the ring is proportional to the concentration of specific immunoglobulin present in the ascites fluid. AI-10 was found to be of class IgG2a and AI-11 was found to be of class IgG1.

Isoelectric profiles of the monoclonal antibodies were obtained by isolectric focusing of 0.01 ml samples of the ascites fluids in 0.8 percent agarose (EF 802-300, LKB-Produkter AB, Bromma, Sweden) containing 10 percent sorbitol, and 2 percent ampholine within a pH value range of 5-8, for 150 minutes at 3 watts constant power. Following fixing and drying, the gels were stained with Coomassie brilliant blue and photographed.

C. Sandwich Assays

1. Apo A-I (HDL) Sandwich ELISA a. Apo A-I Primary Standards: Quantitation of HDL and Isolated Apolipoprotein A-I The HDL fraction (1.063-1.21 g/ml) was obtained from pooled human plasma by standard ultracentrifugation techniques and was dialyzed into PBS. It was then sterile-filtered through a 0.45 micron acrodisc filter unit, and stored at 4 degrees C. The protein content of the HDL fraction was determined by a modified Lowry protein assay with BSA as the standard. Three dilutions of the HDL fraction were run in duplicate to assure readings within a linear part of the standard curve. For example, the HDL fraction was run at dilutions of 1:5, 1:10, and 1:20. Protein concentration was usually between 5 and 10 mg/ml. For extended storage, the HDL fraction was diluted with PBS to a protein concentration of 1-2 mg/ml. After dilution, the protein concentration was again confirmed by Lowry assay at dilutions of 1:2, 1:5, and 1:10. The diluted HDL fraction was then aliquoted and stored at 4 degrees C.

Isolated apolipoprotein A-I can be obtained from a number of commercial sources. Although, the manufacturer typically includes a statement of protein content and purity, the protein concentration was always confirmed by Lowry assay, and adjusted if necessary based on these results. Dilutions of the apo A-I preparation were run as described in the previous section. The preparation was aliquoted and stored as suggested by the manufacturer.

The HDL and/or apo A-I preparations were then assayed as unknown samples (diluted 1:5000) in the apo A-I ELISA (described hereinafter). A minimum of two assay plates per day, containing a complete set of standards, quality controls, and dilutions of the HDL and/or apo A-I preparations were performed over a five day period. The ELISA values obtained for HDL and/or apo A-I agreed within 20% of the Lowry protein assay value. If the values did not agree within the established limits, the Lowry assay was repeated to confirm the assigned protein concentration. If the values were still discrepant, aging or contamination of the preparation was usually indicated, and it is was not deemed suitable for use as a primary standard.

The purity of the primary standard also was determined by analytical sodium dodecyl sulfatepolyacrylamide gel electrophoresis; SDS-PAGE.

b. Apo A-I ELISA Secondary Standard

Preparation and Value Assignment

Preparation of Lyophilized Standard Pooled Plasma

Fresh plasma or serum was collected from at least 10 normolipidemic subjects who had fasted overnight. Phelbotomy was performed using sterile tubes containing disodium EDTA by non-traumatic venipuncture. The samples were centrifuged at 1500 xg for 30 minutes at 4 degrees C., and the plasma was transferred to clean, tightly capped tubes and stored for no more than 24 hours at 4 degrees C. Equal amounts of the samples were combined, and 0.5 ml quantities were aliquotted into acid-cleaned Wheaton 5 ml serum vials, and lyophilized overnight (about 16-18 hours). The vials were sealed and stored at 4 degrees C.

ii. Reconstitution of Lyophilized Pooled Plasma Standard

Vials were allowed to come to room temperature before reconstitution. The aluminum ring and stopper were removed, slowly releasing the vacuum in the vial. Using a precision pipet, the dried, pooled standards were reconstituted with 0.5 ml double distilled water, by slowly dispensing the water to the side of the vials. The stoppers were replaced and the vials were quickly swirled 3-4 times and maintained at room temperature for at least 30 minutes. The standard was not vortexed or agitated strongly, but swirled gently to insure complete solubiiization.

iii. Value Assignment of the Apo A-I Secondary Standard

The apo A-1 value of the lyophilized secondary standard is determined in the apo A-I ELISA using the primary standard (either HDL or apo A-I) as the calibrator. The ELISA assay procedure is described herein.

The lyophilized secondary standard was assayed as an unknown sample in triplicate on a minimum of two assay plates per day for at least 10 days generating a minimum of 20 values (mean of triplicates). All values obtained for the secondary standard were averaged and the apo A-I value in milligrams per deciliter (mg/dl) was assigned.

Once the value assignment had been made, the secondary standard was used to construct a standard curve that was assayed on the same ELISA plate with a primary standard curve, with a complete set of controls. Primary and secondary standard curves were assayed on a minimum of 2 assay 96-well plates per day over a period of 5 days.

Once the value assignment of the secondary standard was accepted, standard curves were constructed and assayed on the same ELISA plate with the currently accepted lot of lyophilized standard over a period of five days (2 assay plates per day).

c. The Assay, Generally

Isolated AI-10 molecules were affixed to the walls of polystyrene microtiter plate wells (Nunc-Immuno Plate 1; Irving Scientific, Santa Ana, Calif.) by admixing 0.15 ml of a pH 9.0 sodium bicarbonate buffer containing 5 micrograms per milliliter (ug/ml) AI-10 into each well. The plates were maintained for 18 hours at 4 degrees C. and then washed 3 times with PBS containing 0.1 percent BSA and 0.05% polyoxyethyelene (20) sorbitan monolaurate (Tween 20). Residual, non-specific binding sites were then blocked by admixing 0.2 ml of PBS containing 10 percent BSA in each well, maintaining the admixture for 1 hour at 37 degrees C., followed by rinsing. Wells so prepared can be used for up to about one month after preparation when stored in a humdified chamber.

Human HDL was diluted in PBS to concentrations ranging from 1.0 to 0.031 ug/ml for use as standard control solutions. As noted before, human HDL rather than human apo A-I is used as a standard in these assays because apo A-I has been found to be relatively unstable on storage while HDL appears to be relatively more storage-stable. Plasma (or serum) samples were diluted 1:5000 in PBS.

Fifty microliters (ul) of standard or sample were admixed in the wells in triplicate. Within about 5 minutes thereafter, 50 ul of PBS containing HRPO-labeled AI-11 paratopic molecules were admixed in each well. The immunoreaction admixtures were maintained for a time period of 30 minutes at 25 degrees C. Nonbound material was then separated from the wells by washing as described above.

The amount of solid phase-affixed sandwich immunoreactant containing HRPO label was then assayed by admixing 0.1 ml of freshly prepared substrate solution [distilled water containing 3 percent $H_2O_2$ and 0.67 mg/ml.

d. Step-wise Apo A-1 HDL Sandwich ELISA

The following steps were carried out in performing the apolipoprotein A-I sandwich ELISA. Commercial controls were reconstituted according to package inserts with deionized water. The controls were swirled gently and maintained 20-30 minutes at room temperature to ensure complete solution.

(i) Samples and Controls

Samples and controls are diluted 1:5000 in PBS. A serial dilution can be made as follows:

20 ul sample + 1.98 ml PBS (1:100);
40 ul of above dilution + 1.96 ml PBS (1:5000).

(ii) Standard Dilution

Isolated apo A-I (HDL) standard is diluted to 4 ug/ml in PBS. Then 2-fold serial dilutions to 0.031 ug/ml are made. For example, using a preparation of HDL designated 860527 that contained 868 ug/ml 4 ug/ml = 46 ul + 9.954 ml PBS (1:217);
2 ug/ml = 1 ml of above + 1 ml PBS; and
Continue 2-fold dilutions to 0.031 ug/ml.

(iii) HRPO-Labeled AI-11 Dilution

A 1:5000 dilution of AI-11 HRPO conjugate antibody in PBS is used. The following dilutions can be made:

20 ul + 1.98 ml PBS (1:100); and
240 ul of above + 11.76 ml PBS (1:5000).

Cover with foil to protect from light. This amount is sufficient for 2 plates.

(iv) 3 Percent Hydrogen Peroxide

Dilute 30 percent hydrogen peroxide ($H_2O_2$) 1:10 in distilled water.

(v) o-Phenylenediamine Substrate

Dissolve 1 o-phenylenediamine (OPD) tablet (Sigma Chemical Co., St. Louis, Miss.) in 15 ml distilled water. Add 62.5 ul 3 percent $H_2O_2$. Cover with foil to protect from light. Make substrate fresh each time just before use.

e. Assay Procedure i. Equilibrate antibody-bound ELISA plate at ambient room temperature (20-22 degrees C.) for at least 20 minutes. Remove plate from bag and invert plate to remove residual buffer in wells. Fill the wells with 300 ul Rinsing Buffer (PBS containing 0.1% BSA and 0.05% Tween 20, pH 7.2) and maintain for a time period of 10 minutes. Invert plate to remove buffer, and blot plate dry on paper toweling. Do not allow wells to sit empty longer than 10 minutes during the assay.

ii. Add 50 ul standard or sample to wells in triplicate. The 0 ug/ml standard is 50 ul of PBS.

Add 50 ul diluted HDL standards to the standard wells (0.031, 0.062, 0.125, 0.25, 0.50, 1.0 ug/ml).

Add 50 ul of diluted controls and patient samples to ther respective wells.

iii. Add 50 ul/well of HRPO-linked antibody to all wells.

iv. Wrap plate in aluminum foil and place on a gyro-shaker (about 100 RPM) for 30 minutes at ambient room temperature (about 20-25 degrees C.).

v. Wash the plate by filling the wells with 300 ul/well of Rinsing Buffer and then inverting the plate to remove the buffer. Repeat two more times for a total of three washes. Blot plate dry on paper toweling after third wash. Do not allow the plate to dry out.

vi. Add 100 ul/well of freshly-prepared OPD substrate. Allow color to develop at room temperature for 30 minutes.

vii. Stop reaction with 50 ul of 4N Sulfuric Acid to all wells. Read O.D. at 492 nm.

2. Apo B-100 Sandwich ELISA a. Plasma Pool Collection and Preparation for Lyophilization for Secondary Standard Collect fresh plasma from 10 normal subjects who have fasted overnight. (Subjects are allowed to drink black coffee or tea.)

Perform phlebotomy using a sterile vacuatiner tube containing Disodium EDTA, by non-traumatic venipuncture techniques. Centrifuge samples at 1500× xg for 30 minutes at 4 degrees C. Transfer plasma to clean, tightly capped tubes and stored for no more than 24 hours.

Combine equal amount of the plasma samples. Aliquot 0.5 ml quantities into chromic acid-cleaned Wheaton 5 ml amber serum bottles (VWR Scientific Division, Univar, San Francisco, Calif.; VWR #223778). Place rubber stoppers onto the bottles so that no more than ¼" on the stopper is inserted into the bottle. Bottles are then placed on the trays that have been removed from the Shelf Unit of the lyophilizer.

b. Lyphilization of the Plasma Pool for the Standard

The system used for lyophilization was FTS Systems Dura-Stop Shelf Unit along with Dura-Dry Condenser Unit. (FTS Systems, Inc., Stone Ridge, N.Y.)

i. Cool Dura-Stop Shelf Unit down to −50° C.

ii. Freeze plasma samples by placing tray with samples in pre-cooled Shelf Unit. Place thermocouple lead detectors inside a few vial samples to monitor temperature changes.

iii. once thermocouple lead detectors indicate that the samples are frozen to −50° C., (approximately 30 minutes, time varies depending on the number of samples) turn on the refrigeration in the Dura-Dry Condenser Unit.

iv. When maximum low temperatue is reached, the vacuum pump is turned on.

v. Once vacuum pressure reaches 200 microns or lower, increase temperature in the Shelf Unit to −20° C.

vi. Leave samples at this temperature for approximately 20 hours at which point the temperature is raised to −10° C.

vii. In 30 minutes, increase the temperature to −50° C. The final temperature increase to 4° C. is performed 30 minutes later.

viii. The shelf in the Shelf Unit is then raised to push the rubber stoppers into the bottles. The vacuum is then broken in the chamber and the samples are removed.

ix. Use a Wheaton hand crimper (Wheaton #224303; VWR Scientific, Division of Univar, San Francisco, Calif. to secure Wheaton aluminum seals (VWR Scientific, VWR #226-355) on the sample vials. The samples are then stored at 4° C. until use.

c. Reconstitution and Stability i. Reconstitution

Lyophilized plasma standards should be at room temperature before reconstitution. A minimum of 30 minutes at room temperature is suggested.

Remove the aluminum ring and stopper, being careful to slowly release the vacuum in the vial. Using a precision pipet, reconstitute with 0.5 ml deionized $H_2O$. Slowly dispense the water to the side of the vial. Replace the stopper, quickly swirl the vial 3-4 times and let stand at room temperature for at least 30 minutes. This standard also is not vortexed nor agitated strongly, but swirled to obtain solution.

After 30 minutes, gently swirl the vial before use.

ii. Stability

The standard is stored between 2-8 degrees C. before and after reconstitution. The reconstituted standard is stable for 4 weeks when so stored.

d. Value Assignment (i) Competitive ELISA

Value assignment for the lyophilized standard is determined in the competitive reference ELISA using a primary LDL. Flexible polyvinyl chloride microtiter plates (Falcon, Microtest III) were coated for 16 hours at 4° C. with 200 ul of PBS containing 5 ug/ml of the LDL. The wells were then washed 3 times with 200 ul of PBS containing 1% BSA, and 0.5% Tween. Residual binding sites were blocked with 200 ul of 3% BSA in PBS for one hour at 25° C. Then the wells were again washed 3 times, using the same washing buffer. For the standard curve, which was included on each plate, the LDL-Apo B-100 standard was diluted in PBS containing 0.5% lipoprotein depleted plasma (LPDP) to provide LDL concentrations ranging from 32 ug/ml to 0.25 ug/ml. In each assay, three different controls were utilized: (1) Isolab Lipotype Control (Akron, Ohio), (2) three levels of Tago Inc. Apolipoprotein B Reference Sera Controls (Burlingame, Calif.), and (3) Omega Lipid Fraction Control Serum (Cooper Biomedical, Malvern, Pa. Each control was prepared according to manufacturer's instructions.

Plasma samples and controls were diluted 200-fold in LPDP/PBS dilution buffer. Fifty ul of the standards, controls, and unknowns were pipetted into the wells, followed immediately by 50 ul of a fixed concentration of MB24 ascites fluid (2000-fold dilution in 3% BSA/PBS). The plates were then incubated 18 hours at 4° C. All determinations were made in triplicate. After again washing the wells, 100 ul of HRPO-conjugated goat anti-mouse IgG diluted 4000-fold in 1% BSA/PBS was added to the wells, incubated for exactly one hour at 25° C., then again washed. The substrate solution contained 3% $H_2O_2$ and 0.67 mg/ml o-phenylenediamine (OPD) (Cat #2781, sigma) diluted in distilled water. One hundred ul of freshly prepared substrate solution containing 3% $H_2O_2$ and 0.67 mg/ml o-phenylenediamine (OPD) in distilled water was added to all wells and color allowed to develop for 30 minutes at 25° C. The reaction was stopped by the addition of 50 ul of 4N $H_2SO_4$, and the optical density (O.D.) of the solution was then determined at 490 nm using a 96 well microtiter plate reader (Dynatech MR600; Alexandria, Va.).

(ii) Apo B-100 Sandwich Assay

The next step is to use the lyophilized standard in the direct sandwich assay. Polystyrene microtiter plates (Nunc-Immuno Plate I) were coated with 150 ul of sodium bicarbonate buffer, pH 9.0, containing 1 ug/ml of purified MB47 for 16 hours at 4° C. The plates were washed 3 times with PBS containing 0.1% BSA, 0.05% Tween, and then blocked with 3% BSA exactly as described for the competition assay. The LDL-apo B lyophilized standard was diluted in 1:200 LPDP/PBS (Diluting buffer) to concentrations ranging from 0.125 to 4.0 ug/ml. The same controls described above for the competition ELISA were used in this assay. Plasma samples and controls were diluted 1000-fold in dilution buffer. Fifty ul of standards, controls, and unknowns were added to the wells in triplicate. Then, 50 ul of PBS containing a fixed concentration of HRPO-linked MB24 was immediately pipetted into all wells. The plates were incubated exactly 30 minutes at 25° C., washed, and 100 ul of OPD substrate solution added for a 30 minute, 25° C. incubation. Color development was stopped by addition of 50 ul of 4N $H_2SO_4$ and plates read in a microplate reader as in the competition ELISA.

D. Competitive ELISA

Reagent apo B-100 in the form of LDL was affixed to the walls of flexible polyvinylchloride microtiter plate wells (Microtest III, Falcon Labware, Becton, Dickinson & Co., Oxnard, Calif.) as solid matrix by admixing 0.2 ml of PBS containing 5 ug/ml of isolated human LDL into each well. The wells were maintained for 16 hours at 4 degrees C., and were then washed 3 times with 0.2 ml of PBS containing 1 percent BSA, 0.5 percent Tween and 0.02 percent aprotinin (Sigma Chemical Co., St. Louis, Miss.). Residual nonspecific binding sites were blocked as described in the noncompetitive ELISA.

Non-specific binding sites were blocked by coating with 3 percent BSA in PBS for 30 minutes at room temperature. Plates were then washed with PBS washing buffer additionally containing 0.1 percent BSA, 0.01 percent sodium azide and 0.05 percent Tween-20.

For the standard curve, which was included on each plate, the reagent LDL was diluted in PBS containing 0.5 percent lipoprotein-depleted plasma (LPDP) to provide concentrations ranging from 32 mg/ml to 0.25 mg/ml.

Plasma samples were diluted 1:200 in PBS containing 0.5 percent LPDP. Fifty microliters of the standards or samples were admixed in triplicate into the wells. Within about 5 minutes thereafter, 50 ul of PBS containing 3 percent BSA and about 4 ug/ml of MB24 paratopic molecules were admixed into each well. The admixtures so formed were maintained for about 18 hours at 4 degrees C. The nonbound material was then separated from the solid phase-affixed MB24-reagent apo B-100 immunoreaction products by washing as described above.

The solid phase immunoreactants were prepared for assaying by admixing 0.1 ml of PBS containing 1 percent BSA and an effective amount of HRPO-labeled goat anti-mouse IgG to each well. This second immunoreaction admixture was maintained for about 1 hour at 24 degrees C. and then washed as described above to form a sandwich immunoreactant.

The amount of solid phase affixed sandwich immunoreactant containing HRPO label was assayed as described in the competitive ELISA.

E. Plasma Samples and Lipoprotein Quantification

Plasma samples were obtained from 20 patients with coronary artery disease from the cardiac catheterization laboratory at the San Diego VA Hospital. In addition, plasma was obtained from 37 normal subjects.

Blood was collected into tubes containing 1.5 mg/ml ethylenediamine tetraacetate (EDTA), and the plasma was separated immediately by centrifugation at 4 degrees C.

Total plasma cholesterol and triglycerides were measured on fresh plasma samples in a standardized clinical laboratory using an Abbott ABA-200 bichromatic analyzer, and Boehringer-Mannheim high performance cholesterol reatent 236691 and Abbott Laboratories triglycerides A-gent. LDL- and HDL-cholesterol were measured using techniques described in *Lipid Research Clinic Procedures*, HEW Pub. No. 75-628 (NIH), 2 ed., Washington, D.C., Gov. Print. Off., (1974). Apoprotein B levels were determined using two commercially available radial immunodiffusion kits: Diffu-gen RID (Tago, Inc., Burlingame, Calif.) which is termed RID I here, and M-Partigen RID, (Calbiochem-Behring, La Jolla, Calif.) which is termed RID II herein.

F. Fluid Phase $^{125}$I-Labeled Antigen RIA

To determine the fraction of $^{125}$I-LDL particles bound by MB47 and MB24, a fluid phase RIA was utilized following the general procedures of Tsao et al. (1982) *J. Biol. Chem.* 257:1,522–15,228. Two different LDL (d=1.019–1.063 gm/ml) preparations were studied, one isolated from pooled plasma of 10 normal subjects and one isolated from plasma of one normal subject.

$^{125}$I-LDL (2000 cpm/ng), prepared using the Iodogen (Pierce Chemical Co., Rockford, Ill.) technique, was 90 percent trichloracetic acid (TCA) precipitable. That composition was diluted in 9 percent bovine serum albumin (BSA) (Sigma, St. Louis, Miss.) and centrifuged at 30,000× xg for 15 minutes prior to each assay to remove complex material.

Assays were performed in 12×75 mm glass tubes in triplicate in 55 mM sodium barbital buffer, at a pH value of 8, containing 150 mM NaCl, 0.02 percent sodium azide, 3 percent BSA, and 1.5 mM sodium-EDTA. To 0.1 ml of $^{125}$I-LDL [containing 20 nanograms (ng) LDL protein] were added 0.1 ml of buffer or competing antigen and 0.1 ml of increasing concentrations of isolated MB47 receptors diluted in the BSA-barbital buffer. After 18 hours at 4 degrees C., 0.1 ml of IgSorb (The Enzyme Co., Boston, Mass.) were admixed. After 2 hours of maintenance time, 2 ml of BSA-free barbital buffer were added, and the tubes were immediately centrifuged at 1,500 xg for 60 minutes. The resulting precipitates were washed twice with barbital buffer.

Assays utilizing AI-10 and AI-11 were carried out similarly, as discussed in Tsao et al. above and in Curtiss and Edgington (1985) *J. Biol. Chem.* 2160:2982–2993. Thus, to 0.1 ml of radiodinated antigen (HDL) or apolipoprotein A-I) were added 0.1 ml of phosphate-buffered saline, pH 7.2, and 0.1 ml of varying dilutions of mouse hybridoma culture fluid or ascites fluid diluted in 1:50 normal mouse serum. All buffers also contained 5% dextran (m.w. 40,000). After 18 hours at 4 degrees C., 0.1 ml of precipitating second antibody (goat anti-mouse IgG serum) was added. Following a 4-hour incubation at 4 degrees C., 2 ml of cold PBS were added, and the tubes were centrifuged at 2000 xg for 30 minutes at 4 degrees C. Supernatants were decanted and the $^{125}$I activity of the pellets determined in a gamma counter.

Maximum precipitable radioactivity was determined by replacing the IgSORB (for MB47) or the second antibody (for AI-10 and AI-11) with 100% TCA. The minimum preciptable radioactivity or non-specific binding (NSB) was determined by replacing the specific hybridoma antibodies with an irrelevant hybridoma antibody of the same heavy chain class.

Data were calculated as:

$$\text{percent of } ^{125}\text{I-antigen bound} = \frac{\text{MEAN} - \text{NSB} \times 100}{\text{TCA} - \text{NSB}}$$

where MEAN=mean radioactivity precipitated in the presence of a given amount of specific antibody and TCA is the maximum TCA-precipitable radioactivity.

D Competitive Immunoenzymometric Assay for AI-10 and AI-11

Flexible polyvinyl chloride microtiter plates were coated for a time period of about 18 hours (overnight) at 4 degrees C. with 0.2 ml of phosphate-buffered saline (PBS) containing 5 ug/ml of either HDL or purified apo A-I. The wells were washed three times with 0.3 ml of PBS containing 1.0 g BSA and 0.5 ml Tween 20 per liter. Residual binding sites on the wells were blocked by incubating 0.2 ml of PBS containing 30 BSA per liter in the wells for 1 hour at ambient temperature (20–25 degrees C.). The wells were then washed three times with rinsing buffer. Plates were used immediately.

PBS (0.05 ml) containing 0.375 ug/ml of AI-10 conjugated with horseradish peroxidase was incubated in the pre-coated wells with 0.05 ml of PBS containing from 0 to 8.0 ug/ml of unconjugated AI-10 or unconjugated AI-11 monoclonal antibody. Incubation time was three hours at ambient temperature (20–25 degrees C.). Wells were then washed three times with rinsing buffer and 0.1 ml of PBS containing o-phenylenediamine substrate was added to all the wells, and incubated for 30 minutes at ambient temperature. The color reaction was stopped by the addition of 0.05 ml of 4N $H_2SO_4$ to all wells, and the optical density (O.D.) of each well was determined at 490 nanometers (nm) using a Dynatech 96-well plate reader.

Figure 3A:
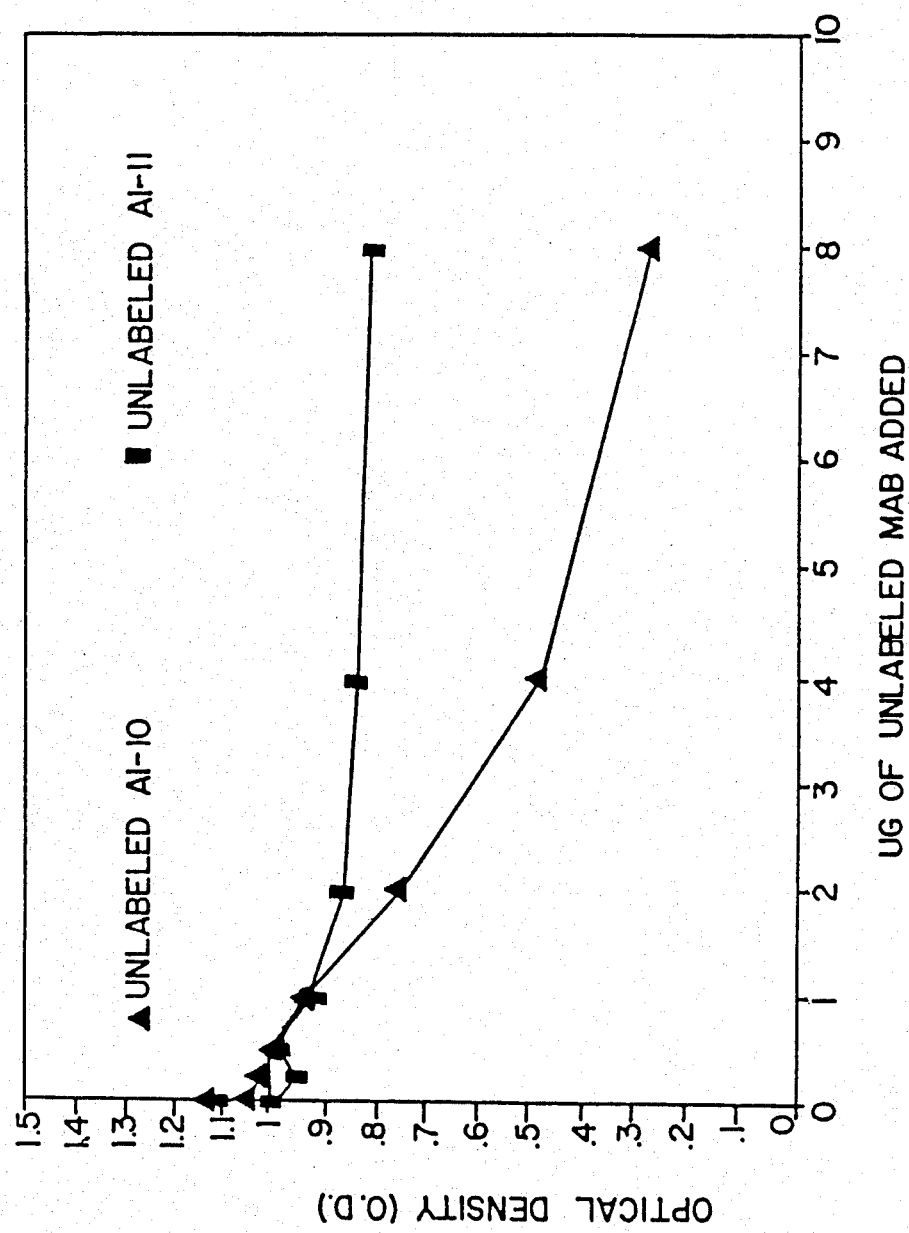
Figure 3B:
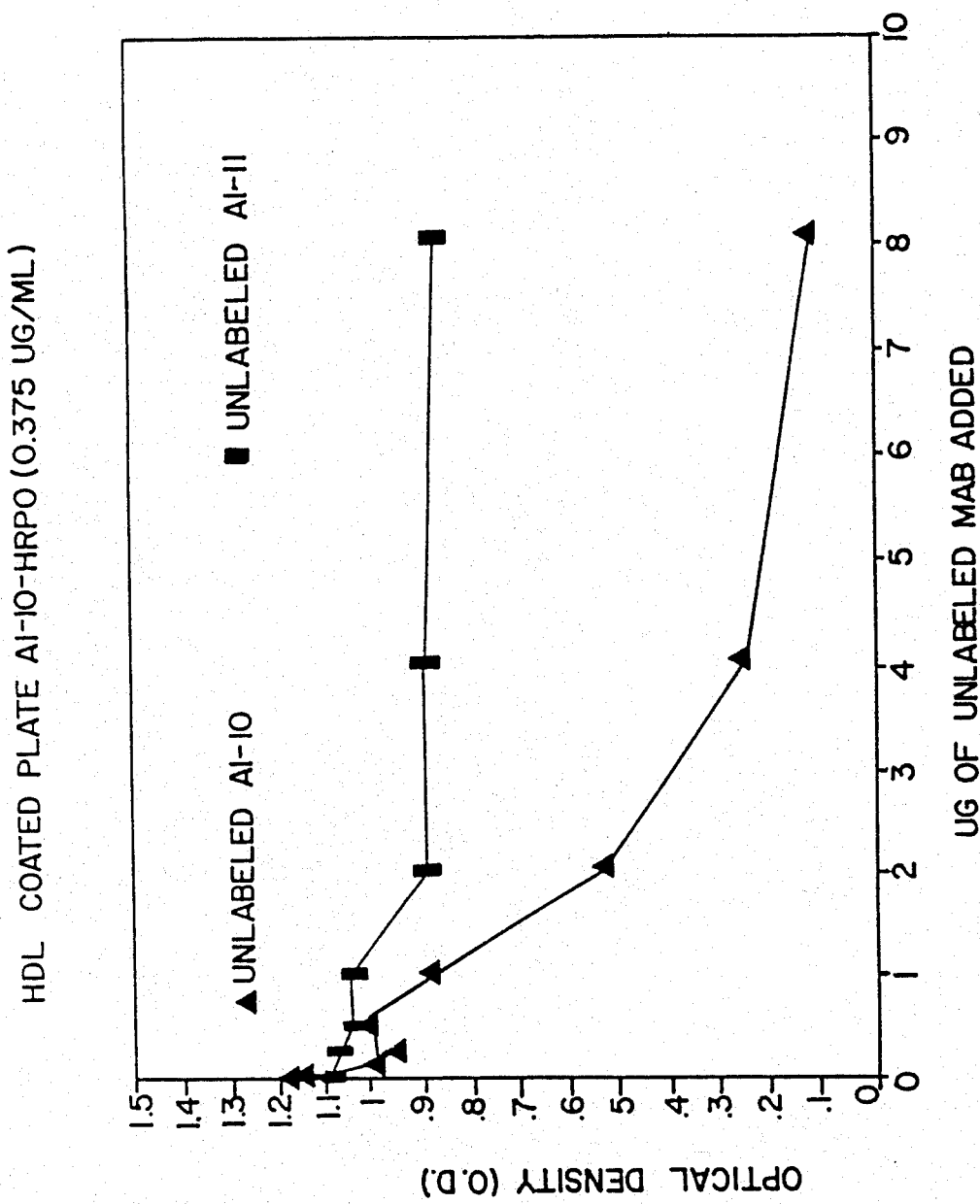

Results of the apo A-I coated plate are shown in FIG. 3A and results of the HDL coated plate are shown in FIG. 3B. A 21-fold increase of unlabeled AI-II molecules did not significantly compete with peroxidase-labeled AI-10 molecules for binding to HDL or apo AI. The study has been repeated using peroxidase-labeled AI-11 with unlabeled AI-10 and AI-11 at the same concentrations with substantially the same results.

The present invention has been described with respect to preferred embodiments. It will be clear to those skilled in the art that modifications and/or variations of the disclosed subject matter can be made without departing from the scope of the invention set forth herein.

What is claimed is:

1. In a method for assaying for a marker of abnormal lipid metabolism comprising the steps of assaying for the amount of human apolipoprotein B-100 and apolipoprotein A-I per unit volume of a blood sample and determining the ratio of apolipoprotein B-100 to apolipoprotein A-I in the sample, the improvement that comprises:

(a) assaying a first aliquot of an apolipoprotein B-100-containing liquid blood sample from a person for the amount of apolipoprotein B-100 present by:
      (i) admixing said first liquid sample aliquot with a solid support consisting essentially of a solid matrix having solid phase-bound first monoclonal paratopic molecules that immunoreact with apolipoprotein B-100 and are secreted by one of the hybridomas having ATCC accession numbers HB 8742 or HB 8746 to form a first solid-liquid phase admixture, the surface of said support having blocked non-specific binding sites;
      (ii) maintaining said first solid-liquid phase admixture under biological assay conditions for a predetermined period of time sufficient for said first paratopic molecules to immunoreact with apolipoprotein B-100 present in the sample aliquot and form a solid phase-bound immunoreactant that contains substantially all apolipoprotein B-100 present in said sample aliquot;
      (iii) admixing apolipoprotein B-100 in said first liquid sample aliquot with liquid phase second monoclonal paratopic molecules that immunoreact with apolipoprotein B-100, are secreted by one of the hybridomas having ATCC accession numbers HB 8742 or HB 8746 but are not utilized in step (a)(i), and are operatively linked to an enzyme indicating means to form a second admixture;
      (iv) maintaining said second admixture under biological assay conditions for a predetermined period of time sufficient for said second indicating means-linked paratopic molecules to form an immunoreactant that contains substantially all apolipoprotein B-100 in the sample aliquot;
      (v) separating the solid and liquid phses that result from above steps (a)(i-iv); and
      (vi) determining the amount of indicating means-linked apolipoprotein B-100-containing immunoreactant present in the separated solid phase, and thereby the amount of apolipoprotein B-100 in a unit volume of sample;

(b) assaying a second aliquot of said liquid blood sample that contains apolipoprotein A-I and is free from unmasking treatment for the amount of apolipoprotein A-I present by:
      (i) admixing said second liquid sample aliquot with a solid support consisting essentially of a solid matrix having solid phase-bound third monoclonal paratopic molecules that immunoreact with apolipoprotein A-I and are secreted by one of the hybridomas having ATCC accession numbers HB 9200 or HB 9201 to form a third, solid-liquid phase, admixture, the surface of said solid support having blocked non-specific binding sites;
      (ii) maintaining said third, solid-liquid phase, admixture under biological assay conditions for a predetermined period of time sufficient for said third paratopic molecules to immunoreact with apolipoprotein A-I present in the aliquot sample and form a solid phase-bound immunoreactant that contains substantially all apolipoprotein A-I in the sample aliquot;
      (iii) admixing apolipoprotein A-I in said second liquid sample aliquot with liquid phase fourth monoclonal paratopic molecules that immunoreact with apolipoprotein A-I, are secreted by one of the hybridomas having ATCC accession numbers HB 9200 or HB 9201 but are not utilized in step (b)(i), and are operatively linked to an enzyme indicating means to form a fourth admixture;
      (iv) maintaining said fourth admixture under biological assay conditions for a predetermined period of time sufficient for said fourth, indicating means-linked paratopic molecules to form an immunoreactant with substantially all apolipoprotein A-I present in the sample aliquot;
      (v) separating the solid and liquid phases that result from steps (b)(i-iv); and
      (vi) determining the amount of indicating means-linked apolipoprotein A-I-containing immunoreactant present in the separated solid phase, and thereby the amount of apolipoprotein A-I in a volume of sample.

2. The method of claim 1 wherein said admixing of steps (a)(i) and (a)(iii) are carried out substantially simulatneously, and said maintaining steps are carried out substantially simultaneously.

3. The method of claim 1 wherein the solid and liquid phases present after step (a)(ii) are separated prior to step (a)(iii), and the apolipoprotein B-100 in said first liquid aliquot admixed in step (a)(iii) is present in the solid phase-bound immunoreactant formed in step (a)-(ii).

4. The method of claim 1 wherein the solid and liquid phases present after step (b)(ii) are separated prior to step (b)(iii ), and the apolipoprotein A-I in said second liquid aliquot admixed in step (b)(iii) is present in the solid phase-bound immunoreactant formed in step (b)(ii).

5. The method of claim 1 wherein said admixing of steps (b)(i) (b)(iii) are carried out substantially simultaneously, and said maintaining steps are carried out substantially simultaneously.

6. In a method for assaying for a marker of abnormal lipid metabolism comprising the steps of assaying for the amounts of human apolipoprotein B-100 and apolipoprotein A-I per unit volume of a blood sample and determining the ratio of apolipoprotein B-100 to apolipoprotein A-I in the sample, the improvement that comprises:

(a) assaying a first aliquot of an apolipoprotein B-100-containing liquid blood sample from a person for the amount of apolipoprotein B-100 present by:
      (i) forming a first solid-liquid phase admixture by substantially simultaneously admixing said first liquid sample aliquot with a solid support consisting essentially of a solid matrix having solid phase-bound first monoclonal paratopic molecules that immunoreact with apolipoprotein B-100 and are secreted by one of hybridomas having ATCC accession numbers HB 8742 or HB 8746 and second monoclonal paratopic molecules operatively linked to an enzyme indicating means that are the secreted by either of hybridomas having ATCC HB accession numbers 8742 or HB 8746 and are not first the paratopic molecules bound to the solid matrix, the surface of said support having blocked non-specific binding sites;

(ii) maintaining said first solid-liquid phase admixture under biological assay conditions for a predetermined period of time sufficient for said first paratopic molecules and said indicating means-linked second paratopic molecules to immunoreact with substantially all apolipoprotein B-100 present in the sample aliquot to form a solid phase-bound sandwich immunoreactant and a liquid phase;

(iii) separating the solid and liquid phases; and (iv) determining the amount of indicating means-linked apolipoprotein B-100-containing sandwich immunoreactant present in the separated solid phase, and thereby the amount of apolipoprotein B-100 in a unit volume of sample;

(b) assaying a second aliquot of said liquid blood sample that contains apolipoprotein A-I and is free from unmasking treatment for the amount of apolipoprotein A-I present by:

(i) forming a second solid-liquid phase admixture by substantially simultaneously admixing said second liquid sample aliquot with a solid support consisting essentially of a solid matrix having solid phase-bound third monoclonal paratopic molecules that immunoreact with apolipoprotein A-I and are secreted by one of hybridomas having ATCC accession numbers HB 9200 or HB 9201 and fourth monoclonal paratopic molecules operatively linked to an enzyme indicating means that are secreted by either of hybridomas having ATCC accession numbers HB 9200 or HB 9201 and are not the third paratopic molecules bound to the solid matrix, the surface of said support having blocked non-specific binding sites;

(ii) maintaining said second solid-liquid phase admixture under biological assay conditions for a predetermined period of time sufficient for said third paratopic molecules and said indicating means-linked fourth paratopic molecules to immunoreact with substantially all apolipoprotein A-I present in the sample aliquot to form a solid phase-bound sandwich immunoreactant and a liquid phase;

(iii) separating the solid and liquid phases; and (iv) determining the amount of indicating means-linked apolipoprotein A-I-containing sandwich immunoreactant present in the separated solid phase, and thereby the amount of apolipoprotein A-I in a unit volume of sample.

7. The method of claim 6 wherein said first paratopic molecules are secreted by the hybridoma having ATCC accession number HB 8746.

8. The method of claim 6 wherein said third paratopic molecules are secreted by the hybridoma having ATCC accession number HB 9200.

9. The method of claim 6 wherein said maintenance under biological assay conditions of steps (a)(ii) and (b)(ii) is for a time period of about 30 minutes to about 60 minutes at ambient room temperature.

10. The method of claim 9 wherein said maintenance is for a time period of about 30 minutes and said first and second solid-liquid phase admixtures are agitated during said time period.

11. A diagnostic system suitable for use in determining the ratio of apolipoprotein B-100 to apolipoprotein A-I in a liquid blood sample comprising:

(a) a first container having paratopic molecules that immunoreact with apolipoprotein B-100 and are secreted by one of the hybridomas having ATCC accession numbers HB 8742 or HB 8746;

(b) a second container having paratopic molecules that immunoreact with apolipoprotein B-100, are secreted by one of the hybridomas having ATCC accession numbers HB 8742 or HB 8746 but are not in the first container, and are opertively linked to an enzyme indicating means;

(c) a third container having paratopic molecules that immunoreact with apolipoprotein A-I and are secreted by one of the hybridomas having ATCC accession numbers HB 9200 or HB 9201; and (d) a fourth container having paratopic molecules that immunoreact with apolipoprotein A-I are secreted by one of the hybridomas having ATCC accession numbers HB 9200 or HB 9201 but are not in the third container, and are operatively linked to an enzyme indicating means;

each of said paratopic molecules being present in an amount sufficient to carry out one determination of said ratio.

12. The diagnostic system of claim 11 wherein the respective monoclonal paratopic molecules that immunoreact with apolipoprotein B-100 and with apolipoprotein A-I that are not linked to said respective indicating means are each separately bound to a solid phase matrix to form separate solid supports, the surface non-specific binding sites of said supports being blocked.

13. The diagnostic system of claim 12 wherein monoclonal paratopic molecules secreted by hybridomas having ATCC accession numbers HB 8746 and HB 9200 are bound to said separate solid matrices.

* * * * *

UNITED STATES PATENT AND TRADEMARK OFFICE
CERTIFICATE OF CORRECTION

PATENT NO. : 4,828,986          Page 1 of 4

DATED : May 9, 1989

INVENTOR(S) : Richard S. Smith et al.

It is certified that error appears in the above-identified patent and that said Letters Patent is hereby corrected as shown below:

Column 3, line 60, delete "physicochemical" and insert --physiochemical--;

Column 4, line 20, delete "constitutents" and insert --constituents--;

Column 6, line 7, delete "diethy" and insert --diethyl--;

Column 8, line 12, delete "-100" and insert --B-100--;

Column 8, line 66, delete "apoliproprotein" and insert --apolipoprotein--;

Column 9, line 28, delete "alliquot" and insert --aliquot--;

Column 9, line 52, delete "ATTC" and insert --ATCC--;

Column 9, line 62, delete "results" and insert --result--;

Column 11, line 43, delete " ◆ " and insert -- ▲ --;

Column 12, line 9, delete " ◆ " and insert -- ■ --;

Column 12, line 30, delete " ◆ " and insert -- ▲ --;

Column 14, line 32, delete "biolgically" and insert --biologically--;

UNITED STATES PATENT AND TRADEMARK OFFICE
CERTIFICATE OF CORRECTION

PATENT NO. : 4,828,986
DATED : May 9, 1989
INVENTOR(S) : Richard S. Smith et al.

It is certified that error appears in the above-identified patent and that said Letters Patent is hereby corrected as shown below:

Column 15, line 51, delete "A-1" and insert --A-I--;

Column 17, line 11, before "$^{125}$I-LDL" insert --(--;

Column 19, line 60, delete "suport" and insert --support--;

Column 24, line 7, delete "laast" and insert --least--;

Column 26, line 44, delete "Apoliprotein" and insert --Apolipoprotein--;

Column 26, lines 66-67, delete "immunoraction" and insert --immunoreaction--;

Column 28, line 7, delete "Immunoglobin" and insert --Immunoglobulin--;

Column 28, line 65, delete "isolelectric" and insert --isoelectric--;

Column 29, line 58, before "Preparation" insert --i.--;

Column 29, line 67, delete "aliquotted" and insert --aliquoted--;

UNITED STATES PATENT AND TRADEMARK OFFICE
CERTIFICATE OF CORRECTION

PATENT NO. : 4,828,986
DATED : May 9, 1989
INVENTOR(S) : Richard S. Smith et al.

It is certified that error appears in the above-identified patent and that said Letters Patent is hereby corrected as shown below:

Column 30, line 20, delete "A-1" and insert --A-I--;

Column 30, line 59, delete "humdified" and insert --humidified--;

Column 31, line 13, at end of sentence add -- ] --;
Column 31, line 54, delete "Miss." and insert --MO--;

Column 32, line 56, delete "once" and insert --Once--;

Column 33, line 9, after "Calif." insert --)--;
Column 33, line 54, after "Pa" insert --)--;

Column 34, line 46, delete "Miss." and insert --MO--;

Column 35, line 29, delete "reatent" and insert --reagent--;
Column 35, line 44, delete "15,228" and insert --1528--;
Column 35, line 54, delete "Miss." and insert --MO--;
Column 35, line 55, delete "30,000 X xg" and insert --30,000xg--;

Column 36, line 5, delete "2160" and insert --260--;

UNITED STATES PATENT AND TRADEMARK OFFICE
CERTIFICATE OF CORRECTION

PATENT NO. : 4,828,986

DATED : May 9, 1989

INVENTOR(S) : Richard S. Smith et al

It is certified that error appears in the above-identified patent and that said Letters Patent is hereby corrected as shown below:

Column 36, line 6, delete "radiodinated" and insert --radioiodinated--;

Column 36, line 6, delete "(HDL)" and insert --(HDL--;

Column 36, line 63, delete "AI-II" and insert --AI-11

Column 37, claim 1, line 50, delete "phses" and insert --phases--;

Column 38, claim 1, line 32, before "volume" insert --unit--;

Column 38, claim 2, lines 34-35, delete "simulatneously" and insert --simultaneously--, Column 38, claim 5, line 50, after "(b)(i)" insert --and--;

Column 39, claim 6, line 5, delete "the";

Column 40, claim 11, line 31, delete "opertively" and insert --operatively--.

Signed and Sealed this

Twelfth Day of June, 1990

Attest:

HARRY F. MANBECK, JR.

Attesting Officer      Commissioner of Patents and Trademarks

UNITED STATES PATENT AND TRADEMARK OFFICE
CERTIFICATE OF CORRECTION

PATENT NO. : 4,828,986
DATED : May 9, 1989
INVENTOR(S) : Richard S. Smith et al.

It is certified that error appears in the above-indentified patent and that said Letters Patent is hereby corrected as shown below:

Column 1, after the heading "TECHNICAL FIELD", insert the following paragraph:

--This invention was made with government support under Contract H 14197 awarded by the National Institutes of Health. The government has certain rights in the invention.--

Signed and Sealed this

Fourth Day of January, 1994

Attest:

BRUCE LEHMAN

*Attesting Officer*  *Commissioner of Patents and Trademarks*